(12) United States Patent
Frisken et al.

(10) Patent No.: US 10,575,724 B2
(45) Date of Patent: Mar. 3, 2020

(54) HIGH RESOLUTION 3-D SPECTRAL DOMAIN OPTICAL IMAGING APPARATUS AND METHOD

(71) Applicant: Cylite Pty Ltd, Notting Hill (AU)

(72) Inventors: Steven James Frisken, Vaucluse (AU); Trevor Bruce Anderson, Melbourne (AU); Armin Georg Segref, Melbourne (AU); Grant Andrew Frisken, Mitcham (AU)

(*) Notice: Subject to any disclaimer, the term of this patent is extended or adjusted under 35 U.S.C. 154(b) by 0 days.

(21) Appl. No.: 15/951,198

(22) Filed: Apr. 12, 2018

(65) Prior Publication Data

US 2018/0228363 A1 Aug. 16, 2018

Related U.S. Application Data

(63) Continuation of application No. 15/166,267, filed on May 27, 2016, now Pat. No. 9,955,863.

(30) Foreign Application Priority Data

May 28, 2015 (AU) .................................. 2015901970

(51) Int. Cl.
*A61B 3/10* (2006.01)
*A61B 3/14* (2006.01)
(Continued)

(52) U.S. Cl.
CPC ............ *A61B 3/0025* (2013.01); *A61B 3/102* (2013.01); *A61B 3/1225* (2013.01); *A61B 3/14* (2013.01);
(Continued)

(58) Field of Classification Search
CPC ........... A61B 3/14; A61B 3/0025; A61B 3/12; A61B 3/102; A61B 3/0008
(Continued)

(56) References Cited

U.S. PATENT DOCUMENTS 9,955,863 B2* 5/2018 Frisken ................ A61B 3/0025
2010/0149487 A1* 6/2010 Ribak ...................... A61B 3/12
351/206

(Continued)

FOREIGN PATENT DOCUMENTS

CN 103815867 A 5/2014

*Primary Examiner* — Mohammed A Hasan
(74) *Attorney, Agent, or Firm* — Darren Gardner

(57) ABSTRACT

Methods and apparatus are presented for obtaining high-resolution 3-D images of a sample over a range of wavelengths, optionally with polarisation-sensitive detection. In preferred embodiments a spectral domain OCT apparatus is used to sample the complex field of light reflected or scattered from a sample, providing full range imaging. In certain embodiments structured illumination is utilised to provide enhanced lateral resolution. In certain embodiments the resolution or depth of field of images is enhanced by digital refocusing or digital correction of aberrations in the sample. Individual sample volumes are imaged using single shot techniques, and larger volumes can be imaged by stitching together images of adjacent volumes. In preferred embodiments a 2-D lenslet array is used to sample the reflected or scattered light in the Fourier plane or the image plane, with the lenslet array suitably angled with respect to the dispersive axis of a wavelength dispersive element such that the resulting beamlets are dispersed onto unique sets of pixels of a 2-D sensor array.

28 Claims, 10 Drawing Sheets

(51) Int. Cl.
  *A61B 3/00*    (2006.01)
  *A61B 3/12*    (2006.01)
  *G06T 11/00*   (2006.01)
  *G02B 27/10*   (2006.01)
  *G06T 15/08*   (2011.01)

(52) U.S. Cl.
  CPC ........ *G06T 11/008* (2013.01); *G02B 27/1013* (2013.01); *G06T 15/08* (2013.01)

(58) Field of Classification Search
  USPC ....................................................... 351/206
  See application file for complete search history.

(56) References Cited

U.S. PATENT DOCUMENTS

| | | |
|---|---|---|
| 2011/0096294 A1 | 4/2011 | Peymann |
| 2012/0140173 A1 | 6/2012 | Uhlhorn |
| 2013/0195446 A1* | 8/2013 | Zheng ................. H04B 10/506 398/34 |
| 2013/0301001 A1 | 11/2013 | Carnevale |
| 2016/0135679 A1* | 5/2016 | Frisken ................ A61B 3/0025 351/212 |

\* cited by examiner

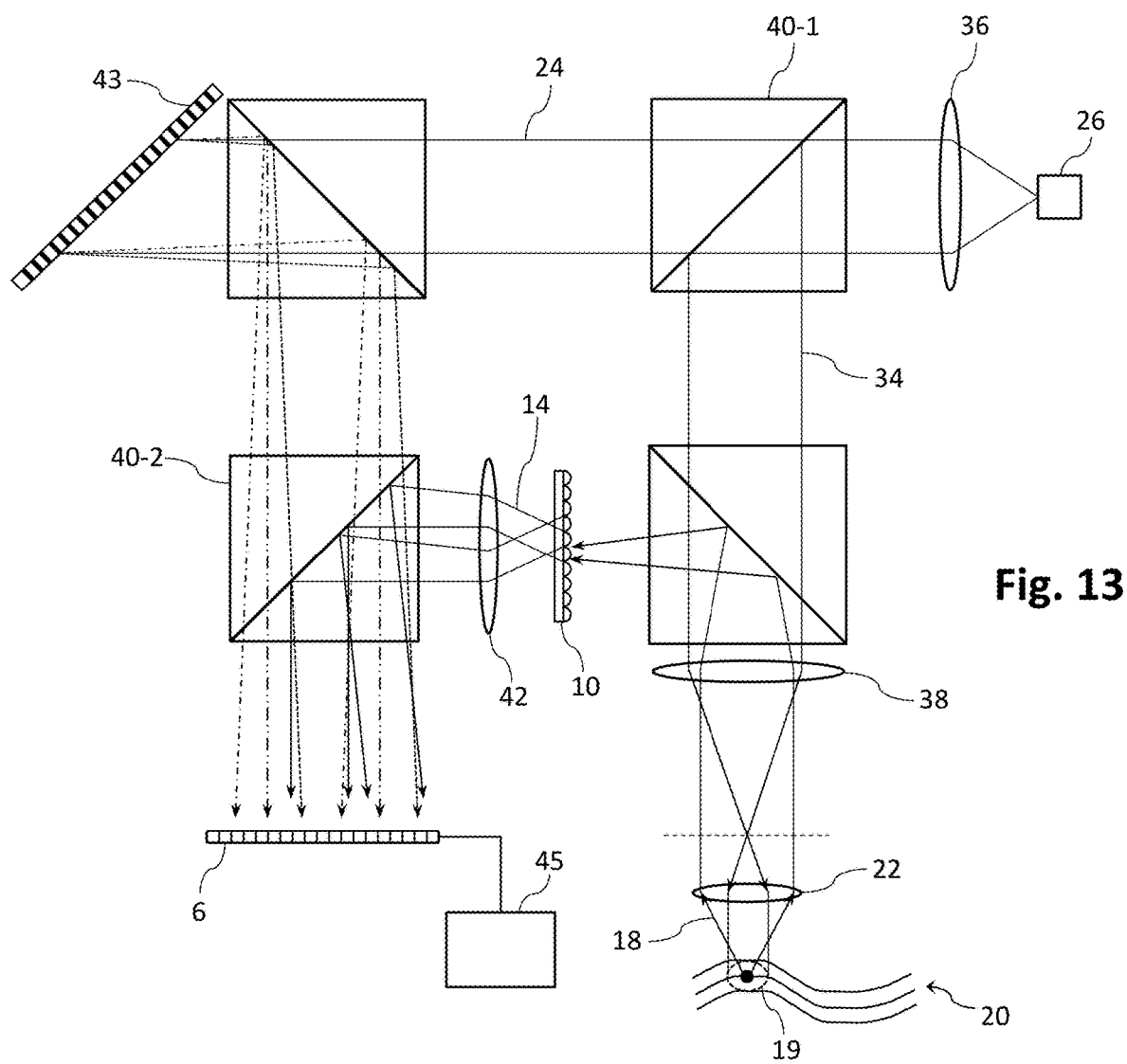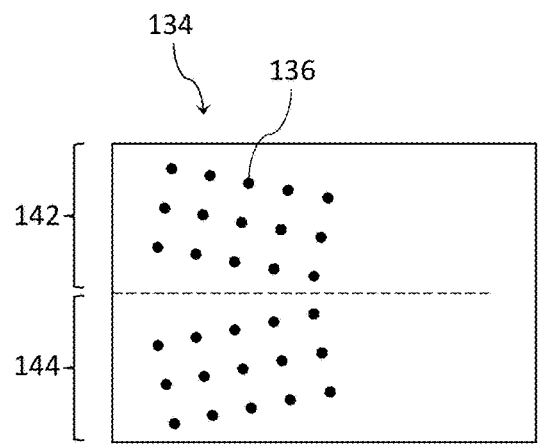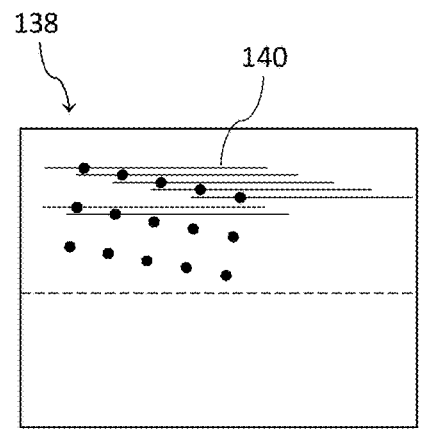
Fig. 13
Fig. 13A
Fig. 13B

HIGH RESOLUTION 3-D SPECTRAL DOMAIN OPTICAL IMAGING APPARATUS AND METHOD

RELATED APPLICATIONS

The present application is a continuation of U.S. Pat. No. 9,955,863 dated 1 May 2018, the entire contents of which are incorporated herein by reference. The present application claims priority from Australian Provisional Patent Application No 2015901970 entitled 'High resolution 3-D spectral domain optical imaging apparatus and method' filed on 28 May 2015, the contents of which are incorporated herein by reference.

FIELD OF THE INVENTION

The invention relates to optical imaging apparatus and methods, and in particular to a 3-D spectral domain optical coherence tomography (OCT) apparatus with full range and extended depth of focus that samples the complex field. However it will be appreciated that the invention is not limited to this particular field of use.

BACKGROUND OF THE INVENTION

Any discussion of the prior art throughout the specification should in no way be considered as an admission that such prior art is widely known or forms part of the common general knowledge in the field.

Optical coherence tomography (OCT) is a widely used interferometric technique for studying biological samples including in vivo tissue such as the human eye, with lateral and depth resolution, using information contained within the amplitude and phase of reflected or scattered light. OCT systems generally utilise a Michelson interferometer configuration, with two main approaches being employed: time domain OCT and spectral domain OCT.

In time domain OCT coherence properties of a partially coherent source such as a superluminescent light emitting diode (SLED) with a coherence length of several microns are utilised by interfering light reflected from a sample with a reference beam provided by the same source, but with a time-varying path length. At a specific depth in the sample corresponding to the path length delay in the reference arm, an interference envelope of fringes will be detected in the combined back-reflected signal, allowing the reflection profile in the depth dimension to be reconstructed. Commonly this is done for only a single sample point at a time, and the corresponding scan of depth is known as an 'A-scan'.

Instead of scanning a delay line, spectral domain OCT techniques analyse the reflected light by interfering it with a reference beam, either as a time-varying function of wavelength (swept source OCT) or by dispersing the different wavelengths with a grating or other spectral demultiplexer and detecting them simultaneously along a detector array. The spectral domain information is the Fourier transform of the spatial (depth) reflection profile, so the spatial profile can be recovered by a Fast Fourier Transform (FFT). Generally speaking, spectral domain OCT systems are preferred over time domain OCT systems because they have a ~20 to 30 dB sensitivity advantage.

OCT techniques can be adapted to provide a laterally resolved 'B-scan' by scanning the sample beam relative to the sample in one axis, or a 'C-scan' by scanning in two axes. Faster acquisition is generally desirable irrespective of the type of scan, especially for reducing motion-induced artefacts with in vivo samples, and has been greatly improved over the previous 20 to 25 years by advances in several fields including faster swept source scanning rates and photodetector array readout speeds. However a fundamental limitation with scanning spot schemes, especially for in vivo applications, is presented by laser safety regulations: reducing dwell time to increase scanning speed without being able to increase the applied power will inevitably degrade the signal to noise ratio.

Consequently there has also been research into 'parallelised' OCT systems in which an extended sample area is probed with lateral resolution, or an array of sample spots probed simultaneously. It is relatively straightforward to parallelise time domain OCT, e.g. by utilising a CCD camera and imaging optics as described in U.S. Pat. No. 5,465,147 entitled 'Method and apparatus for acquiring images using a CCD detector array and no transverse scanner'. This provides a two dimensional (2-D) en face image, with depth resolution provided by scanning the reference mirror as usual in time domain OCT.

Swept source spectral domain OCT can be parallelised in similar fashion, as described in Bonin et al 'In vivo Fourier-domain full-field OCT of the human retina with 1.5 million A-lines/s', *Optics Letters* 35(20), 3432-3434 (2010). However because each frame corresponds to a single wavelength, the acquisition time for each A scan is equal to the frame period times the number of k-points (wavelength samples) acquired. Even for very high speed cameras with frame rates of 100s of kHz, this can lead to A scan acquisition times of many ms which can lead to motion artefacts especially with in vivo samples. PCT patent application No PCT/AU2015/050788, entitled 'Multichannel optical receivers', discloses an alternative parallelised swept source OCT scheme that enables faster acquisition. In one particular implementation a plurality of spots on a sample are illuminated simultaneously and the reflected or scattered signal light mixed with a reference beam to form a plurality of interferograms with unique carrier frequencies.

Parallelised spectrometer-based spectral domain OCT enables single shot B-scan acquisition, although existing schemes are limited by the fact that one axis of a 2-D photodetector array is occupied by the wavelength dispersion. In a configuration described in published US patent application No 2014/0028974 A1 entitled 'Line-field holoscopy', cylindrical lenses are used to produce a line illumination on a sample and on a reference mirror. As shown schematically in FIG. 1, the combined return sample and reference beams from a line illumination 2 are dispersed with a dispersive element such as a grating 4 and detected with a 2-D sensor array 6. A Fourier transform along the spectral axis 8 provides an A-scan for each position 9 along the illuminated line 2. For full three-dimensional (3-D) imaging the illuminated line is mechanically scanned in the orthogonal direction and the 2-D sensor array read out repeatedly.

Even if a linear B-scan of a sample is sufficient, i.e. 3-D imaging isn't required, a scan in the orthogonal direction may still be necessary, e.g. for digital wavefront correction to correct for lens aberrations and the like, or to provide increased depth of field. Furthermore for these purposes the repeated linear scans have to be phase coherent, which is generally difficult.

It is generally preferred for spectral domain OCT apparatus to be configured to sample the unambiguous complex field of the interference signal, rather than just the detected real-valued interference signal, to distinguish positive and negative path length delays and therefore enable imaging over the full depth of field range. A variety of approaches for capturing the complex field have been described. For example Jungwirth et al 'Extended in vivo anterior eye-segment imaging with full-range complex spectral domain optical coherence tomography', *Journal of Biomedical Optics* 14(5), 050501 (2009) describes, for a scanning spot scheme, a solution in which the sample phase is dithered as the sample is scanned. A key drawback of this approach is that sample movement can cause loss of phase coherence during scanning. Line field systems, which have improved phase stability, have been described which do not require dithering of the sample phase. In US 2014/0028974 A1 for example the complex field is obtained by sampling the signal in the far field of a linear illumination, whilst in Huang et al 'Full-range parallel Fourier-domain optical coherence tomography using a spatial carrier frequency', *Applied Optics* 52(5), 958-965 (2013), the line field is captured in the image plane, with an off-axis reference providing access to the complex field.

The transverse resolution of an OCT apparatus is determined, for a given wavelength, by the numerical aperture of the objective lens. However increasing the numerical aperture of the objective invariably reduces the depth of field, resulting in a trade-off between transverse resolution and depth of field. A variety of software-based or digital focusing techniques have been proposed to overcome this trade-off to increase the depth of field. These approaches generally assume that the phase coherence between scattering points is maintained during scanning and sample collection, and the field may be captured in the image plane or the Fourier plane.

In one example, synthetic aperture techniques are discussed in Mo et al 'Depth-encoded synthetic aperture optical coherence tomography of biological tissues with extended focal depth', *Optics Express* 23(4), 4935-4945 (2015). In another example, the forward model (FM) approach of Kumar et al 'Numerical focusing methods for full field OCT: a comparison based on a common signal model', *Optics Express* 22(13), 16061-16078 (2014), involves sampling the 3-D captured interferometric signal I(x, y, k) in the image plane using a full field swept source OCT apparatus with a 2-D CMOS camera. An unambiguous phase is obtained by requiring the sample to be on one side only of the zero delay, and the defocus correction is achieved by applying a numerical phase correction based on a Fresnel wavefront propagation model. This numerical phase correction is achieved by first performing a 1-D FFT of the real valued signal along the spectral axis to give the complex field, I(x, y, k)→E(x, y, $\Delta z$). This is followed by a 2-D FFT of the lateral coordinates for all positive delays, E(x, y, $\Delta z$)→E($k_x$, $k_y$, $\Delta z$). The Fresnel correction for defocus correction is then applied: E($k_x$, $k_y$, $\Delta z$)→E($k_x$, $k_y$, $\Delta z$)$\gamma$,
where $$\gamma = \exp\left(i\frac{\lambda_0 \Delta z M^2}{4\pi n}(k_x^2 + k_y^2)\right).$$

Here, the wavelength is replaced by the centre wavelength $\lambda_0$, n is the refractive index of the sample and M is the magnification of the OCT apparatus. A 2-D inverse FFT (IFFT) with respect to the spatial frequencies of the phase-corrected field gives an image focused over the full volume.

Digital focusing with a full-range line-field OCT system has been demonstrated in Fechtig et al 'Full range line-field parallel swept source imaging utilizing digital refocusing', *Journal of Modern Optics* (2014), DOI: 10.1080/09500340.2014.990938. In this case the sample field is measured in the image plane and full range measurements are achieved by using an off-axis configuration of the reference arm. This off-axis configuration introduces a lateral carrier frequency which shifts the interference term in frequency space enabling the positive and negative frequency components to be separated, thereby enabling measurement of the complex signal. Phase noise in the scanning direction restricts the digital focusing to one dimension, which is applied to each successive B scan. The complex signal is obtained by first taking a 1-D FFT along the spatial axis corresponding to the off-axis reference, after which a filter can be applied to select the positive frequency signal component from its complex conjugate artefact and the non-interferometric background. A 1-D IFFT then gives a signal measurement with unambiguous phase. Digital focusing is achieved by performing a 1-D FFT along the spectral axis followed by a 1-D FFT of the lateral coordinates to give E($k_x$, $\Delta z$), where $\Delta z$ now extends over the full range. Multiplication by the 1-D phase correction factor followed by a 1-D IFFT gives the focused B-scan over the full range.

A full-field swept source OCT system with sampling in the far field is described in Hillmann et al 'Holoscopy—holographic optical coherence tomography', *Optics Letters* 36(13), 2390-2392 (2011). In this system, 2-D interferograms for each wavelength are propagated to a specific delay $\Delta z$. A 1-D FFT along the spectral axis is then used to reconstruct the focused object for this depth $\Delta z$. This process is repeated for a range of delays and the refocused regions are then stitched together. Full range imaging with sampling in the Fourier plane has been demonstrated using an off-axis reference beam to obtain an unambiguous phase, as described in Hillmann et al 'Efficient holoscopy image reconstruction', *Optics Express* 20(19), 21247-21263 (2012). This numerical post-processing approach, in which the 3-D signal is interpolated onto a non-equally spaced grid, provides a volume image with a resolution equivalent to the focal plane resolution throughout an extended portion of the volume. A final 3-D FFT then gives the focused volume image. Similar methods are used in inverse synthetic aperture microscopy (ISAM), described for example in Ralston et al 'Interferometric synthetic aperture microscopy', *Nature Physics* 3(2), 129-134 (2007).

We note that the approaches described above assume a simple model for depth-dependent defocus. An alternative approach that compensates for unknown optical aberrations using sub-aperture correlations is described in Kumar et al 'Subaperture correlation based digital adaptive optics for full field optical coherence tomography', *Optics Express* 21(9), 10850-10866 (2013).

An important limitation of full-field OCT systems, compared to point-scanning systems, is that that they are susceptible to crosstalk from multi-path scattering and hence have reduced sensitivity. In addition, the lack of confocal filtering increases the susceptibility to spurious reflections from outside the coherence length of the system. The line field approach of US 2014/0028974 A1 partially alleviates these limitations compared to that of a full field system by confocal gating in one axis. An alternative approach to mitigating crosstalk is to use a spatially incoherent source.

Unless the context clearly requires otherwise, throughout the description and the claims the words 'comprising', 'comprises' and the like are to be construed in an inclusive sense as opposed to an exclusive or exhaustive sense. That is, they are to be construed in the sense of 'including, but not limited to'.

OBJECT OF THE INVENTION

It is an object of the present invention to overcome or ameliorate at least one of the limitations of the prior art, or to provide a useful alternative. It is an object of the present invention in a preferred form to provide spectral domain OCT apparatus and methods for acquiring 3-D images of a sample employing single shot acquisition techniques. It is another object of the present invention in a preferred form to provide apparatus and methods for obtaining improved high resolution optical images of a retina based on numerical reconstruction of the spectral characteristics of light reflected or scattered from a small volume of the retina, with correction of aberrations present in the sample eye.

SUMMARY OF THE INVENTION

According to a first aspect of the present invention there is provided an apparatus for retinal imaging, said apparatus comprising:
(i) a multi-wavelength optical source;
(ii) an angularly variable illumination system for directing at least two portions of light emitted from said optical source onto each of two or more volumes of the retina of a sample eye;
(iii) a measurement system for receiving signals of light reflected or scattered from each of said two or more volumes, each said signal being a function of the phase and amplitude of the electric field vector of the reflected or scattered light, and for making simultaneous measurements over a range of wavelengths for each of said signals; and
(iv) a processor for processing the measurements to generate one or more numerical representations of an optical characteristic of said retina over said two or more volumes, and to create from said one or more numerical representations a three-dimensional composite image over a region of said retina comprising at least a portion of said two or more volumes.

According to a second aspect of the present invention there is provided an apparatus for imaging a sample, said apparatus comprising:
(i) a multi-wavelength optical source;
(ii) an illumination system for sequentially directing at least two portions of light emitted from said optical source onto each of two or more volumes of a sample, said sample being located at or close to a focal plane of an optical power element of said apparatus;
(iii) a measurement system for receiving signals of light reflected or scattered from each of said two or more volumes, each said signal being a function of the phase and amplitude of the electric field vector of the reflected or scattered light, and for making simultaneous measurements over a range of wavelengths for each of said signals; and
(iv) a processor for processing the measurements to generate one or more numerical representations of an optical characteristic of said sample over said two or more volumes, and to create from said one or more numerical representations a three-dimensional composite image of said sample over a region comprising at least a portion of said two or more volumes.

The first and second aspects share a number of preferments. Preferably, the processor is adapted to create the three-dimensional composite image using digital refocusing or digital correction of aberrations of the sample eye or of the sample. In certain embodiments the processor is adapted to generate numerical representations of the optical characteristic over each of the two or more volumes, and to create the three-dimensional composite image from the numerical representations. In other embodiments the processor is adapted to generate a numerical representation of the optical characteristic over the two or more volumes, and to create the three-dimensional composite image from the numerical representation.

In certain embodiments the illumination system is adapted to sequentially direct the at least two portions of light onto the two or more volumes of the retina. In other embodiments the illumination system is adapted to simultaneously direct the at least two portions of light onto the two or more volumes of the retina.

The measurement system preferably comprises a two-dimensional lenslet array for sampling the signals and a wavelength dispersive element for dispersing the sampled signals onto a two-dimensional sensor array, wherein the lenslets of the lenslet array are positioned with respect to the wavelength dispersive element such that, in use, each of the sampled signals is dispersed onto a set of pixels of the sensor array. In certain embodiments the two-dimensional lenslet array is positioned so as to sample the signals in the Fourier plane. Preferably, the two-dimensional lenslet array comprises a rectilinear array of lenslets angled with respect to the dispersive axis of the wavelength dispersive element.

Preferably, adjacent pairs of the two or more volumes are partially overlapping. In certain embodiments the processor is adapted to reduce the three-dimensional composite image to a high resolution B scan of the retina or sample.

In certain embodiments the optical characteristic is selected from the group comprising phase, reflectivity, refractive index, refractive index changes and attenuation. In certain embodiments the measurement system is adapted to capture phase and amplitude information for at least first and second polarisation states of the signals. In these embodiments the optical characteristic may comprise birefringence or degree of polarisation.

For each of the two or more volumes the illuminated surface of the retina or sample is preferably less than or equal to 500 µm×500 µm in area, more preferably less than or equal to 200 µm×200 µm in area.

According to a third aspect of the present invention there is provided a relative phase-sensitive optical coherence tomography apparatus comprising:
(i) an imaging system for acquiring first and second images of an optical characteristic of a region of a sample in three spatial dimensions, each said image comprising phase and amplitude information over a range of wavelengths and each being acquired in a single exposure, said second image being acquired a predetermined time period after said first image; and
(ii) a processor for:
(a) registering said first image to said second image to determine a spatially resolved phase shift caused by motion or distortion of said sample in any spatial dimension; and
(b) determining from said phase shift at least a component of the displacement of said sample associated with said motion or distortion.

The processor is preferably adapted to determine from the phase shift and the predetermined time period a rate of displacement of the sample associated with the motion or distortion. In certain embodiments the processor is adapted to measure strain associated with the distortion of the sample, or to perform elastography measurements on the sample.

According to a fourth aspect of the present invention there is provided a polarisation-sensitive optical coherence tomography apparatus comprising:
- (i) an illumination system comprising a multi-wavelength optical source for illuminating a volume of a sample with light of at least a first polarisation state;
- (ii) an optical splitter for directing a portion of light reflected or scattered from said sample away from said optical source;
- (iii) a measurement system for making a first set of simultaneous measurements over a range of wavelengths, for at least first and second polarisation states, of a signal of light reflected or scattered from said sample, said signal being a function of the phase and amplitude of the electric field vector of the reflected or scattered light; and
- (iv) a processor for processing said first set of simultaneous measurements to generate a three-dimensional representation of one or more polarisation properties of the illuminated volume of said sample.

Preferably, the one or more polarisation properties comprises birefringence or degree of polarisation.

In certain embodiments the illumination system is adapted to subsequently illuminate the volume of the sample with light of a second polarisation state, different from the first polarisation state, and the measurement system is adapted to make a second set of simultaneous measurements over a range of wavelengths. In these embodiments the processor is preferably adapted to process the first and second sets of simultaneous measurements to generate a three-dimensional representation of one or more polarisation properties of the illuminated volume of the sample.

In preferred embodiments the optical splitter comprises a polarisation independent beam splitter. Preferably, the optical splitter comprises an apertured reflector having a total internal reflection surface and one or more apertures that locally disrupt the total internal reflection at the surface, for allowing transmission of light for illuminating the sample. More preferably, the apertured reflector comprises two total internal reflection surfaces spaced apart by one or more localised index matching regions that form the one or more apertures.

According to a fifth aspect of the present invention there is provided an optical coherence tomography apparatus for imaging a sample over an extended depth of field, said apparatus comprising:
- (i) an illumination system adapted to illuminate, with beams incident at two or more incident angles and each having at least first and second wavelengths, a volume of a sample to be imaged in three spatial dimensions;
- (ii) an interferometer adapted to measure, over said at least said first and second wavelengths, and in a single shot at least for each incident angle, a two-dimensional grid of sampling points of the phase and amplitude of light reflected or scattered from the volume of the sample illuminated at said two or more incident angles; and
- (iii) a processor for: registering and stitching together in the Fourier Domain the measurements from the two or more incident angles to create an extended Fourier Field of measurements; and generating a three-dimensional image of an optical characteristic of the sample by Fourier Transformation or digital processing of the extended Fourier Field measurements.

In certain embodiments the illumination system is adapted to illuminate the sample volume sequentially with the beams incident at two or more incident angles. In alternative embodiments the illumination system is adapted to illuminate the sample volume simultaneously with the beams incident at two or more incident angles.

In preferred embodiments the interferometer comprises: a two-dimensional lenslet array for providing the two-dimensional grid of sampling points; a two-dimensional sensor array; and a wavelength dispersive element for dispersing the light from each of the sampling points onto the sensor array, wherein the lenslets of the lenslet array are positioned with respect to the wavelength dispersive element such that, in use, the light from each of the sampling points is dispersed onto a set of pixels of the sensor array. In certain embodiments the two-dimensional lenslet array is positioned so as to sample the signals in the Fourier plane. The two-dimensional lenslet array preferably comprises a rectilinear array of lenslets angled with respect to the dispersive axis of the wavelength dispersive element. In preferred embodiments the lateral resolution of the three-dimensional image is enhanced by the extended Fourier Field measurements.

According to a sixth aspect of the present invention there is provided a high resolution optical imaging apparatus, comprising:
- (i) an illumination system for illuminating, with a multi-wavelength optical beam, a volume of a sample to be imaged in three spatial dimensions;
- (ii) a sampling system for sampling in the Fourier plane light reflected or scattered from the illuminated volume of said sample;
- (iii) a measurement system for simultaneous capture of phase and amplitude information over a range of wavelengths of the sampled reflected or scattered light; and
- (iv) a processor for processing the phase and amplitude information to construct a three-dimensional image of an optical characteristic of said sample over said illuminated volume.

In a preferred form the processor is adapted to construct the three-dimensional image using digital refocusing or digital correction of aberrations of the sample.

In preferred embodiments the measurement system comprises a wavelength dispersive element for dispersing the sampled signals obtained from the sampling system onto a two-dimensional sensor array, wherein the sampling system is positioned with respect to the wavelength dispersive element such that, in use, each of the sampled signals is dispersed onto a set of pixels of the sensor array. The sampling system preferably comprises a two-dimensional lenslet array for sampling the reflected or scattered light to provide a two-dimensional grid of sampling points.

In certain embodiments the optical characteristic is selected from the group comprising phase, reflectivity, refractive index, refractive index changes and attenuation. In certain embodiments the measurement system is adapted to capture phase and amplitude information for at least first and second polarisation states of the reflected or scattered light. In these embodiments the optical characteristic may comprise birefringence or degree of polarisation.

The illuminated surface corresponding to the illuminated volume is preferably less than or equal to 500 µm×500 µm in area, more preferably less than or equal to 200 µm×200 µm in area. In preferred embodiments the three-dimensional image has a spatial resolution of 3 µm or better.

According to a seventh aspect of the present invention there is provided a method for imaging the retina of a sample eye, said method comprising the steps of:

(i) providing a multi-wavelength optical beam;
(ii) directing, with an angularly variable illumination system, at least two portions of said multi-wavelength optical beam onto each of two or more volumes of the retina of a sample eye;
(iii) receiving signals of light reflected or scattered from each of said two or more volumes, each said signal being a function of the phase and amplitude of the electric field vector of the reflected or scattered light;
(iv) making simultaneous measurements over a range of wavelengths for each of said signals; and
(v) processing the measurements to generate one or more numerical representations of an optical characteristic of said retina over said two or more volumes, and to create from said one or more numerical representations a three-dimensional composite image over a region of said retina comprising at least a portion of said two or more volumes.

According to an eighth aspect of the present invention there is provided a method for imaging a sample, said method comprising the steps of:
(i) providing a multi-wavelength optical beam;
(ii) sequentially directing at least two portions of said multi-wavelength optical beam onto each of two or more volumes of a sample;
(iii) receiving signals of light reflected or scattered from each of said two or more volumes, each said signal being a function of the phase and amplitude of the electric field vector of the reflected or scattered light;
(iv) making simultaneous measurements over a range of wavelengths for each of said signals; and
(v) processing the measurements to generate one or more numerical representations of an optical characteristic of said sample over said two or more volumes, and to create from said one or more numerical representations a three-dimensional composite image of said sample over a region comprising at least a portion of said two or more volumes.

According to a ninth aspect of the present invention there is provided a method for performing relative phase-sensitive optical coherence tomography measurements of a sample, said method comprising the steps of:
(i) acquiring first and second images of an optical characteristic of a region of a sample in three spatial dimensions, each said image comprising phase and amplitude information over a range of wavelengths and each being acquired in a single exposure, said second image being acquired a predetermined time period after said first image;
(ii) registering said first image to said second image to determine a spatially resolved phase shift caused by motion or distortion of said sample in any spatial dimension; and
(iii) determining from said phase shift at least a component of the displacement of said sample associated with said motion or distortion.

According to a tenth aspect of the present invention there is provided a method for performing polarisation-sensitive optical coherence tomography measurements of a sample, said method comprising the steps of:
(i) illuminating a volume of a sample with multi-wavelength light of at least a first polarisation state;
(ii) directing a portion of light reflected or scattered from said sample away from the source of said multi-wavelength light;
(iii) making a first set of simultaneous measurements over a range of wavelengths, for at least first and second polarisation states, of a signal of light reflected or scattered from said sample, said signal being a function of the phase and amplitude of the electric field vector of the reflected or scattered light; and
(iv) processing said first set of simultaneous measurements to generate a three-dimensional representation of one or more polarisation properties of the illuminated volume of said sample.

According to an eleventh aspect of the present invention there is provided a method for performing optical coherence tomography imaging of a sample over an extended depth of field, said method comprising the steps of:
(i) illuminating, with beams incident at two or more incident angles and each having at least first and second wavelengths, a volume of a sample to be imaged in three spatial dimensions;
(ii) measuring interferometrically, over said at least said first and second wavelengths, and in a single shot at least for each incident angle, a two-dimensional grid of sampling points of the phase and amplitude of light reflected or scattered from the volume of the sample illuminated at said two or more incident angles;
(iii) registering and stitching together in the Fourier Domain the measurements from the two or more incident angles to create an extended Fourier Field of measurements; and
(iv) generating a three-dimensional image of an optical characteristic of the sample by Fourier Transformation or digital processing of the extended Fourier Field measurements.

According to a twelfth aspect of the present invention there is provided a method for performing high resolution optical imaging of a sample, said method comprising the steps of:
(i) illuminating, with a multi-wavelength optical beam, a volume of a sample to be imaged in three spatial dimensions;
(ii) sampling in the Fourier plane light reflected or scattered from the illuminated volume of said sample;
(iii) simultaneously capturing phase and amplitude information over a range of wavelengths of the sampled reflected or scattered light; and
(iv) processing the phase and amplitude information to construct a three-dimensional image of an optical characteristic of said sample over said illuminated volume.

According to a thirteenth aspect of the present invention there is provided an article of manufacture comprising a computer usable medium having a computer readable program code configured to operate the apparatus according to any one of the first to sixth aspects, or to implement the method according to any one of the seventh to twelfth aspects.

According to a fourteenth aspect of the present invention there is provided an apertured reflector comprising: a total internal reflection surface for reflecting light; and one or more apertures that locally disrupt the total internal reflection at said surface, for transmitting light without reflection.

Preferably, the apertured reflector comprises two total internal reflection surfaces spaced apart by one or more localised index matching regions that form the one or more apertures. More preferably, the apertured reflector comprises two prisms with polished optical surfaces that form the two total internal reflection surfaces, fixedly attached and spaced apart from each other with localised regions of an index matched adhesive that form the one or more apertures. The two total internal reflection surfaces are preferably spaced apart by approximately 10 μm.

BRIEF DESCRIPTION OF THE DRAWINGS

Preferred embodiments of the invention will now be described, by way of example only, with reference to the accompanying drawings in which:

FIG. 13 illustrates a linear OCT apparatus configured for image plane sampling of light scattered or reflected from a sample, according to an embodiment of the present invention;

FIG. 13A shows, for a given wavelength, a 2-D FFT of an interferogram obtained with the apparatus of FIG. 13;

FIG. 13B shows a 2D-FFT for dispersed wavelengths of an interferogram obtained with the apparatus of FIG. 13;

DETAILED DESCRIPTION OF THE INVENTION

It will be evident from the foregoing description of the prior art that single shot acquisition of OCT data is advantageous not only for enhanced speed, especially for reducing motion artefacts with in vivo samples, but also for retaining phase coherence for digital refocusing or digital wavefront correction. Acquisition schemes for digital reconstruction of the complex field that are not single shot, i.e. that require multiple readouts of a sensor array, face the difficulty of ensuring phase registration between the data in each of the multiple frames. This difficulty is not insurmountable, but does require additional computation e.g. for stitching together single shot images acquired from adjacent sample volumes.

Figure 1:
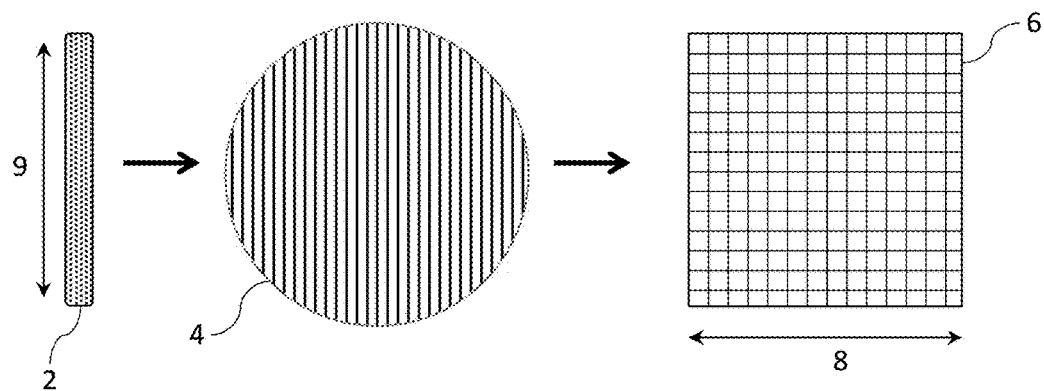
FIG. 1 illustrates in schematic form the acquisition of B-scan data with a 2-D sensor array in a prior art line-field OCT system.

Existing spectrometer-based spectral domain OCT systems, such as that described in US 2014/0028974 A1, can acquire B-scans (one lateral dimension) in a single shot, but not single shot C-scans (two lateral dimensions). This is because one axis of the 2-D sensor array is occupied by the wavelength dispersion, as shown in FIG. 1. This limitation can be overcome if the combined returning sample and reference wavefronts are sampled in the two lateral dimensions with a sampling system that may for example comprise a 2-D lenslet array, a MEMS mirror array or a diffractive optical element (DOE), and the resulting sampling points dispersed onto separate sets of pixels of a 2-D sensor array. The effect of this general scheme is to squeeze data from three spatial dimensions, equivalent to two lateral dimensions and one spectral dimension, onto a 2-D sensor array. The mapping of dispersed sampling points onto separate sets of pixels can be ensured by appropriate orientation or positioning of the sampling points, e.g. the lenslets of a 2-D lenslet array, with respect to the wavelength dispersive element. As shown schematically in FIG. 2, one particular way of implementing this general scheme is to sample the combined wavefronts with a 2-D lenslet array 10 comprising a rectilinear (X, Y) array of lenslets tilted at an angle θ with respect to the dispersive axis 11 of the dispersive element 4 that disperses the beamlets 14-1, 14-2 etc onto a 2-D sensor array 6. Provided the tilt angle is chosen judiciously and the sensor array has sufficiently fine pixels 12, as shown in a partial cutaway view, each beamlet 14-1, 14-2 etc from the lenslet array can be dispersed, e.g. by a grating 4, onto a unique set of pixels 16-1, 16-2 etc of the sensor array, thereby enabling single shot C-scan acquisition.

Another way of expressing the general requirement for obtaining a preferred unique mapping is for the projection 13 of the sampled beamlets onto the sensor array 6 to be suitably angled with respect to the projection of the dispersive axis 11 of the dispersive element 4 onto the sensor array. Other solutions, e.g. using 2-D lenslet arrays with non-rectilinear arrangements of lenslets, will occur to those skilled in the art.

Ideally, the wavelength dispersive element 4 and sensor array 6 are arranged such that the projection of the dispersive axis 11 onto the sensor array is parallel to rows of pixels 12 in the sensor array, i.e. parallel to an axis of the sensor array as shown. In practice however, the dispersed images formed on the sensor array from each beamlet will generally have some degree of curvature such that the mapping, while known, is unlikely to correspond to single rows of pixels over an extended length.

The systems to be described below are generally designed to illuminate a small contiguous area of a sample with a multi-wavelength collimated or near-collimated optical beam of the order of 100 μm in diameter at the sample, and to capture an image of the interaction volume in a single snapshot with spatial resolution significantly better than the size of the illuminated area, e.g. around 3 μm or better. In preferred embodiments the contiguous illuminated area is kept relatively small, less than or equal to 500 µm×500 µm in area, more preferably less than or equal to 200 µm×200 µm in area. This is generally necessitated by the available number of sampling points, i.e. the number of lenslets in commercially available lenslet arrays, but it also reduces the impact of multiple scattering that can severely degrade the resolution of full field, wavelength sequential apparatus. The phase coherence between scatterers in the sample enables accurate volume reconstruction with digital correction of aberrations and an extended depth of focus. Larger lateral ranges can be achieved by scanning the illumination area, e.g. by laterally scanning the beam or the sample, and stitching together sequentially captured volumes, preferably with adjacent volumes partially overlapping to facilitate accurate phase registration. Importantly, the simultaneous illumination of a contiguous area reduces the sensitivity to crosstalk from multi-path scattering and to spurious reflections from outside the coherence length.

In preferred embodiments the 3-D snapshots are captured with a grating-based spectral OCT system, in which a 2-D lenslet array samples the light reflected or scattered from a small contiguous illuminated area, and the resulting beamlets dispersed and imaged onto a 2-D sensor. Importantly, the resolution (number of pixels) of the sensor is much larger than the resolution of the lenslet array (number of lenslets), thus enabling both lateral and spectral information to be captured on the 2-D sensor in a single snapshot. As described above regarding FIG. 2, in preferred embodiments a 2-D rectilinear lenslet array is tilted with respect to the dispersive axis of the dispersive element to ensure that each beamlet is dispersed onto a unique group of pixels. A significant advantage of grid-based sampling is that it enables the use of a simple imaging system, with no requirement for a high magnification 'microscope' to match the sample illumination area to the 2-D sensor. Such a microscope would typically require a magnification of order 100, which demands complicated imaging optics. The reflected or scattered field can be sampled by the lenslet array in either the Fourier plane, i.e. the far field, which is a form of holoscopy, or in the image plane, i.e. the near field. For either case the lateral resolution is determined by the numerical aperture of the objective lens, and the lateral area captured in a single snapshot is determined by the product of the lateral resolution and the number of lenslets. Advantageously, sampling in the Fourier plane allows subsequent processing to recreate an imaging lens mathematically, with the possibility of varying that lens for different parts of a sample.

Full range imaging can be achieved by mixing the signal with an off-axis reference beam to introduce a spatial carrier, enabling unambiguous phase measurement. Given a phase coherent signal, sampled over both transverse axes and wavelength, a number of well-known digital refocusing techniques can be applied. For example techniques developed for swept source holoscopy can be applied to extend the depth of field or to compensate for aberrations.

Figure 2:
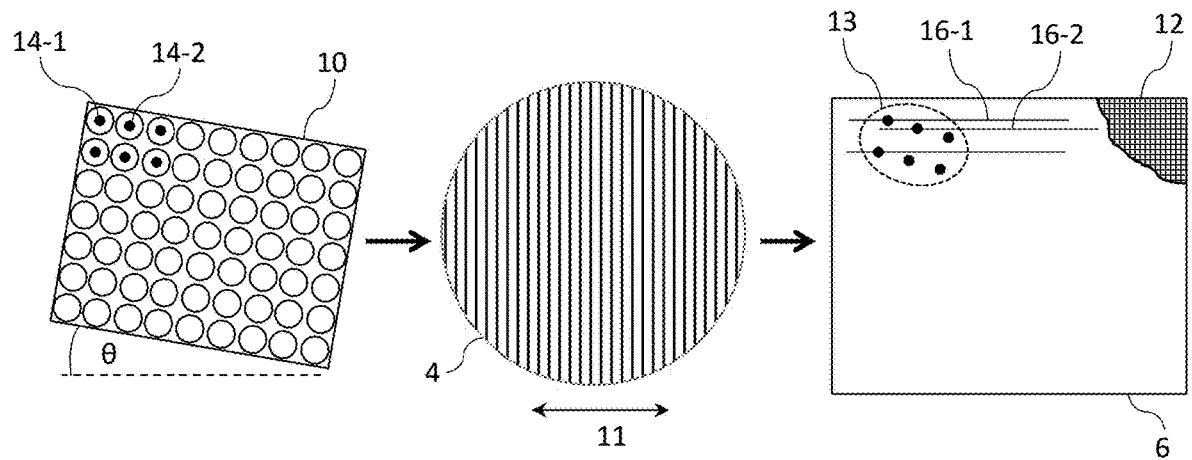
FIG. 2 illustrates a general scheme for mapping data from three spatial dimensions, equivalent to two lateral dimensions and one spectral dimension, onto a 2-D sensor array.

We turn now to description of various 3-D spectral domain OCT systems that exploit the tilted lenslet array technique shown in FIG. 2 for single shot C-scan acquisition, e.g. over regions of up to 500 µm×500 µm in area and with lateral resolution of 3 µm or better. These systems are capable of full range imaging, i.e. the ability to distinguish positive and negative path length delays, wavefront correction such as digital refocusing and aberration correction, and enhanced resolution. Critically, the ability to capture the complex field in a single snapshot ensures that phase coherence is maintained throughout the sample volume, which is a requirement for accurate wavefront correction.

In certain embodiments the combined beams are sampled in the far field, i.e. in the Fourier plane. As illustrated schematically in FIG. 3, light 18 reflected or scattered from a point (x',y') in a contiguous illuminated volume 19 of a sample 20 is collected with an objective lens 22, mixed with an off-axis reference beam 24 and sampled in the Fourier plane with a 2-D lenslet array 10. In this configuration the sample 20, and preferably also the lenslet array 10, are approximately at a focal plane of the objective 22, recognising that a three-dimensional sample cannot be exactly at the focal plane throughout its entire depth. After passing through an aperture array 25 the focused beamlets 14 are collimated, dispersed and imaged onto a 2-D sensor array 6. The aperture array 25 is optional, but serves to block scattered signals from outside the coherence length that would otherwise degrade the sensitivity of the apparatus. As explained previously, in preferred embodiments a rectilinear 2-D lenslet array 10 is tilted with respect to the dispersive axis of the wavelength dispersive element to provide a mapping of the dispersed beamlets onto unique sets of pixels 16-1, 16-2 etc of the sensor array 6. Since the reflected or scattered signal 18 is sampled in the Fourier plane, its lateral content is obtained from the spatial (lateral) frequency content of the sampled signal. The axial reflectivity profile of the interaction volume 19 is encoded in the spectral frequency content, as is usual in spectral domain OCT. Importantly, a spatial Fourier transform separates the positive and negative components of the signal. A subsequent Fourier transform along the spectral axis 8 provides the full range reflectivity profile. A number of optical characteristics of the sample can be extracted with spatial resolution from this reflectivity profile, including for example phase, reflectivity, refractive index, refractive index changes and attenuation. If the measurement system is polarisation sensitive, i.e. adapted to capture phase and amplitude information for at least first and second polarisation states of the beamlets, then one or more polarisation-related optical characteristics such as birefringence or degree of polarisation can be extracted. Many if not all of these optical characteristics will generally be wavelength-dependent.

Figure 4:
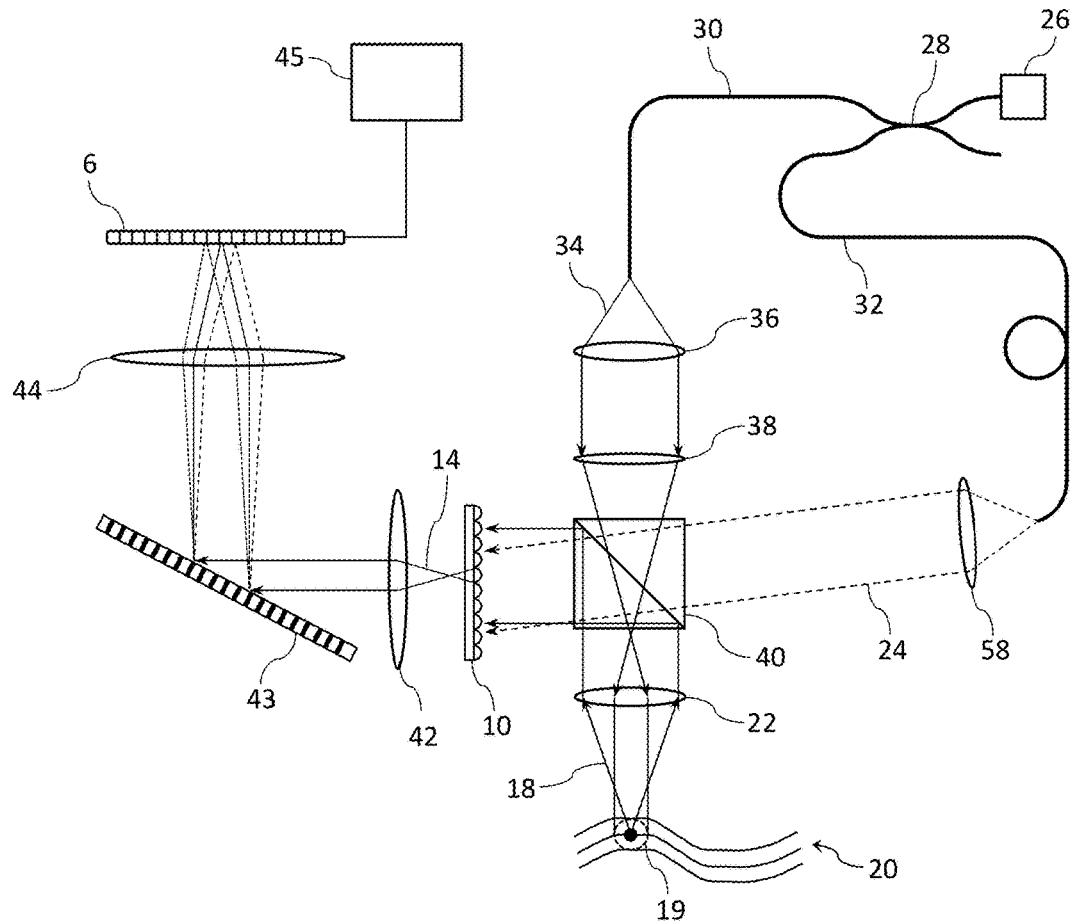
FIG. 4 illustrates a spectral domain OCT apparatus configured for Fourier plane sampling of light scattered or reflected from a sample, according to an embodiment of the present invention.

FIG. 4 shows a spectral domain OCT apparatus configured for Fourier plane sampling of light reflected or scattered from a sample 20, with high lateral resolution. In an illumination system of the apparatus, light from an optical fibre-coupled multi-wavelength or broadband source 26 such as a superluminescent light emitting diode (SLED) is split with a 2×2 optical fibre coupler 28 into a sample arm 30 and a reference arm 32. The splitting ratio of the 2×2 coupler may for example be 90/10 sample/reference, or even 99/1, because in many practical applications the reflectivity of the sample 20 will be low. The sample beam 34 is collimated with a lens 36 then directed onto a sample 20 via a converging lens 38 and an objective 22. In preferred embodiments the objective has a relatively high numerical aperture to ensure high lateral spatial resolution. For example a 0.16 NA objective typically provides a lateral spatial resolution of 3.0 µm. The purpose of the converging lens 38 is to enable illumination of an extended contiguous volume 19 of the sample, for example 100 µm in diameter. Since the sample 20 is at a focal plane of the objective 22, if this converging lens were omitted the illuminated region would be a diffraction-limited spot rather than an extended region. It will be appreciated that a single lens could be used in place of the collimating lens 36 and the converging lens 38.

In a measurement system of the apparatus, reflected or scattered sample light 18 from within the illuminated volume 19 is collected with the objective 22 and directed to a beam splitter such as a beam-splitting cube 40 where it is mixed with an off-axis collimated reference beam 24. The combined beam is sampled in the Fourier plane with an appropriately positioned rectilinear 2-D lenslet array 10, optionally followed by an aperture array (not shown), and the resulting beamlets 14 are collimated with a lens 42, dispersed with a wavelength dispersive element in the form of a reflective grating 43, and focused via a lens 44 onto a 2-D sensor array 6, from which the combined interferogram can be read out in a single frame for subsequent analysis by a processor 45 equipped with suitable machine-readable program code. Alternatively, the dispersive element could be a transmissive grating or a prism. As described above in relation to FIG. 2, the lenslet array 10 is preferably tilted with respect to the dispersive axis of the grating 43 so that each beamlet is mapped onto a unique set of pixels of the sensor array 6. In one particular embodiment the lenslet array has 1000 lenslets in a rectilinear 40×25 grid with a 300 μm pitch, and the 2-D sensor array is a 20 Megapixel CMOS camera with a pixel size of 5.5 μm.

The combined interferogram read out from the sensor array 6 represents a wavelength-dependent measurement of a signal of light reflected or scattered from the interaction volume 19, where the signal is a function of the phase and amplitude of the electric field vector of the reflected or scattered light 18. Using mathematical techniques described below, these wavelength-dependent measurements can be processed to generate numerical representations or construct a three-dimensional image of an optical characteristic of the sample with spatial resolution over at least a portion of the interaction volume 19. A number of optical characteristics of the sample can be extracted, including for example phase, reflectivity, refractive index, refractive index changes and attenuation. Many if not all of these optical characteristics will generally be wavelength-dependent. We note that the measurement system could be made polarisation sensitive, e.g. by inclusion of a polarisation walk-off element in front of the 2-D sensor array 6 as described below with reference to FIG. 14. In this case one or more optical characteristics related to polarisation properties of the sample, such as birefringence or degree of polarisation, could also be extracted.

Figure 5:
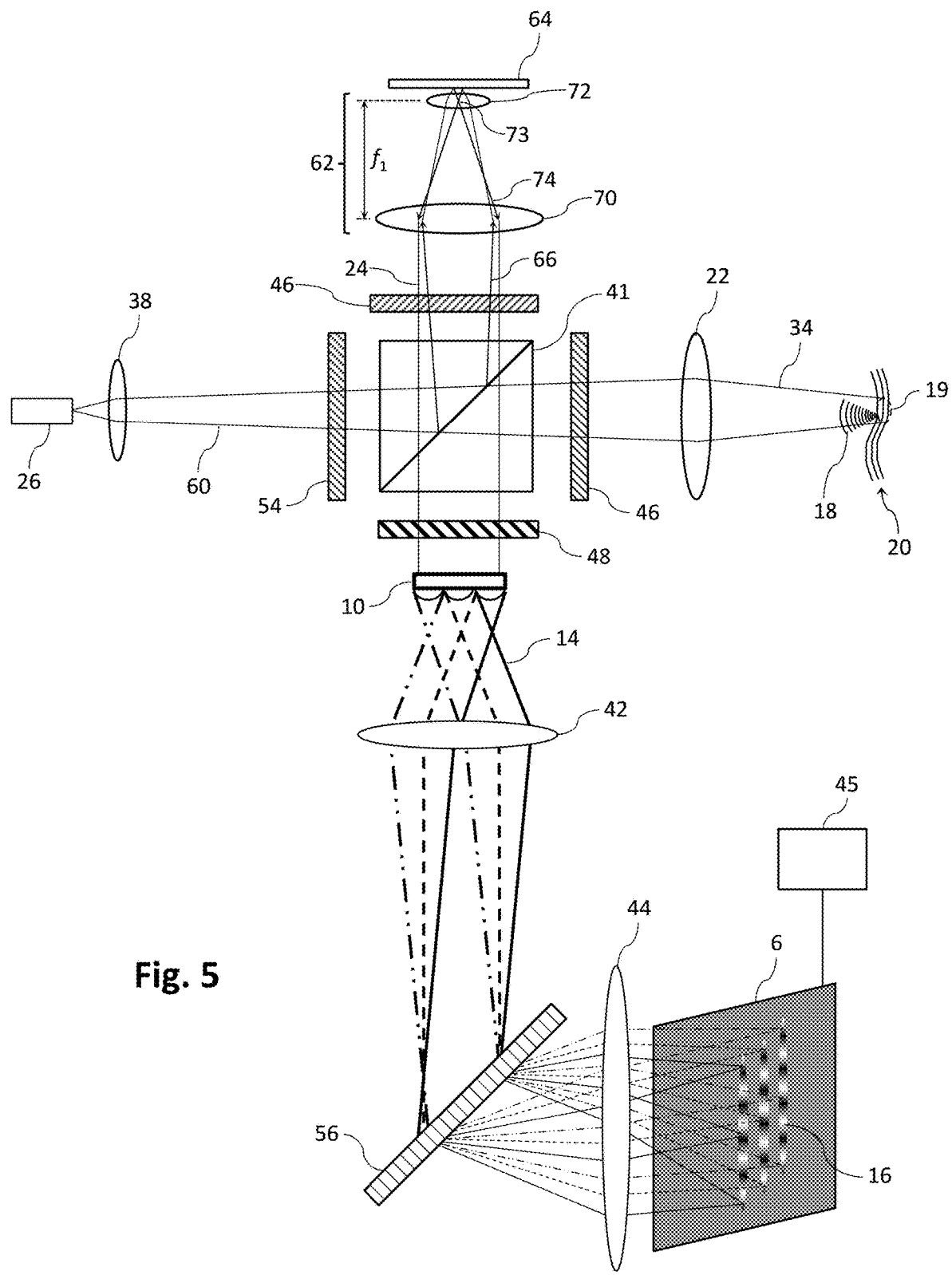
FIG. 5 illustrates another spectral domain OCT apparatus configured for Fourier plane sampling of light scattered or reflected from a sample, according to an embodiment of the present invention.
Figure 6:
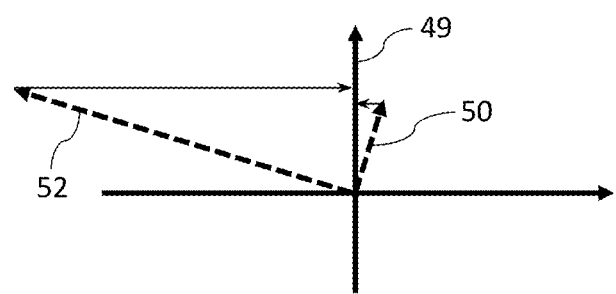
FIG. 6 shows a scheme for reducing the loss of sample power that occurs when analysing the polarisation of a reference beam and a returning sample beam.

FIG. 5 shows another spectral domain OCT apparatus configured for Fourier plane sampling of light reflected or scattered from a sample 20, with high lateral resolution. In this apparatus the sample beam 34 and reference beam 24 are generated and combined with a polarisation beam splitter 41, quarter waveplates 46 and a polarisation analyser 48. An advantage of using a polarisation beam splitter and associated polarising optics instead of a power beam splitter 40 as shown in the FIG. 4 apparatus is that it avoids wasting 50% of the light from the broadband source 26. As mentioned previously the reference beam 24 will generally be much more intense than the returning sample beam 18. One method for compensating for this, as shown in FIG. 6, is to orient the polarisation analyser such that its transmission axis 49 is close to parallel to the polarisation direction 50 of the low intensity returning sample beam, and therefore close to orthogonal to the polarisation direction 52 of the much more intense reference beam. Compared to the usual practice of orienting the polarisation analyser at 45° to the polarisation directions of both beams, this reduces the loss in sample power from 3 dB to less than 1 dB. Returning to FIG. 5, better equalisation of the reference and returning sample beam powers can also be achieved with an optional quarter waveplate 54 in the source arm, oriented such that the polarisation beam splitter 41 preferentially directs the source light 60 into the sample arm.

A combination of a converging lens 38 and a high NA objective 22 is used to illuminate an extended contiguous volume 19 of a sample 20, for example 100 μm in lateral diameter, similar to the case with the apparatus shown in FIG. 4. Reflected or scattered sample light 18 from within the illuminated volume 19 is collected with the objective 22, mixed with the reference beam 24 and sampled in the Fourier plane with an appropriately positioned rectilinear 2-D lenslet array 10 followed by an optional aperture array (not shown). The beamlets 14 are collimated with a lens 42, dispersed with a wavelength dispersive element in the form of a transmissive grating 56, and focused via a lens 44 onto a 2-D sensor array 6. Alternatively, the dispersive element could be a reflective grating or a prism. As described above in relation to FIG. 2, the rectilinear lenslet array 10 is preferably tilted with respect to the dispersive axis of the grating 56 so that each beamlet is mapped onto a unique set of pixels 16 of the sensor array 6. The combined interferogram can be read out from the 2-D sensor array in a single frame for subsequent analysis by a processor 45 equipped with suitable machine-readable program code. Again the interferogram represents a wavelength-dependent measurement of a signal of light reflected or scattered from the illuminated volume 19, where the signal is a function of the phase and amplitude of the electric field vector of the reflected or scattered light 18. As before, these wavelength-dependent measurements can be processed to generate numerical representations or construct a three-dimensional image of an optical characteristic of the sample with spatial resolution over at least a portion of the interaction volume 19.

It is generally preferable to interfere the returning sample beam with a reference beam that is well collimated and covers all of the lenslets in the array 10. This is straightforward in the FIG. 4 apparatus with appropriate selection of the reference arm collimating lens 58, but more difficult in the FIG. 5 apparatus because the source beam 60 entering the beam splitter 41 is intentionally not collimated so as to illuminate an extended (not diffraction-limited) area of the sample 20. To this end the reference arm of the FIG. 5 apparatus includes a NA convertor 62 between the quarter waveplate 46 and the reference mirror 64 to convert a smaller diameter divergent beam 66 into a larger diameter collimated beam 24. The NA convertor 62 comprises a larger diameter lens 70 and a smaller diameter lens 72 (such as a lenslet) separated by a distance equal to the focal length of the larger lens, $f_1$. These two lenses, in combination with the reference mirror 64, bring the divergent beam 66 to a focus 73 inside the lenslet 72. Consequently the lenslet has no refractive power on the return path, so that the outgoing beam 74 with increased NA is collimated by the larger lens 70.

We turn now to a description of an analysis of interferometric data obtained when sampling in the Fourier plane. With Fourier plane sampling, every beamlet 14 contains phase and amplitude information from every point in the interaction volume 19, but at different discrete angles. Spatial information is therefore encoded as angular information.

Figure 3:
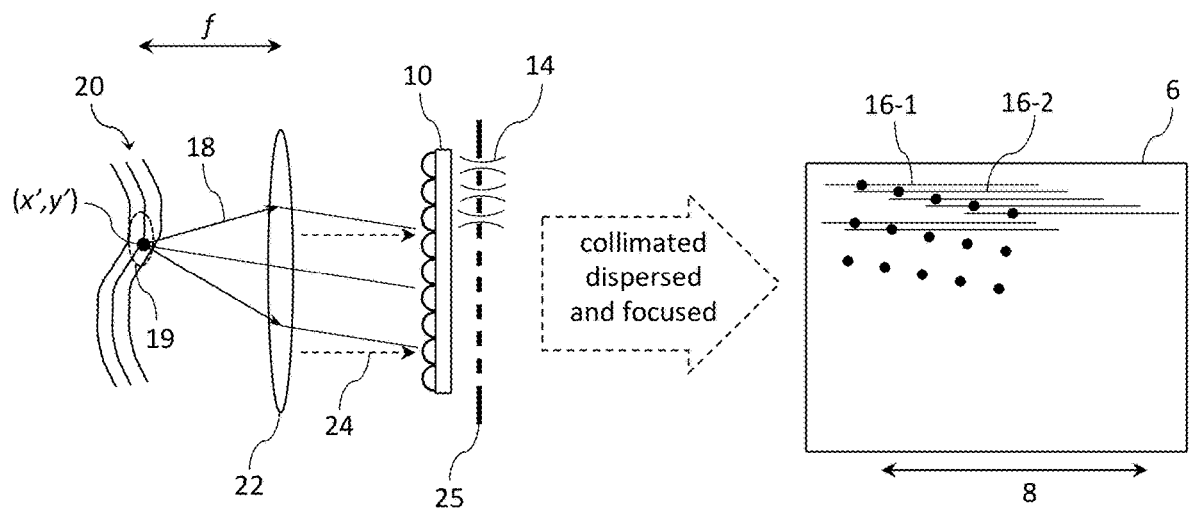
FIG. 3 illustrates an embodiment of the FIG. 2 scheme with sampling in the Fourier plane.

For simplicity we consider the scattering or reflection from a single point at position (x',y') as shown in FIG. 3, and with depth Δz. Assuming that the scattering or reflection point is close to the focal plane of the objective lens 22, the collimated field incident upon the lenslet array 10 will be a plane wave with an incident angle x'/f. The interferometric signal incident on the lenslet array at position X, Y can thus be expressed as:

$$I(X, Y, x', y') = S(k)R(x', y')^{1/2}\cos\left(k\left(\Delta z + \frac{X(x' - x_0)}{f} + \frac{Y(y' - y_0)}{f}\right)\right) \quad (1)$$

where R(x',y') is the sample reflectivity, S(k) is the spectral power distribution, f is the focal length of the objective lens 22, and $x_0$ and $y_0$ are related to the angle of the reference beam 24 with respect to the axis of the objective lens (or to the axis of the lenslet array 10).

To first order, the interferometric signal component at the aperture array 25 for the lenslets (of circular aperture) can be approximated by:

$$I(X_i, Y_j, x', y') = \quad (2)$$
$$S(k)R(x', y')^{1/2}\left(\cos\left(k\left(\Delta z + \frac{X(x' - x_0)}{f} + \frac{Y(y' - y_0)}{f}\right)\right) \otimes circ(X, Y, D)\right)\bigg|_{X=X_i, Y=Y_j}$$

where $X_i$, $Y_j$ describe the axis of the lenslet, D is the pitch of the lenslet array, and $circ(X,Y,D)=1$ for $X^2-Y^2<(D/2)^2$ and 0 otherwise.

Figure 7:
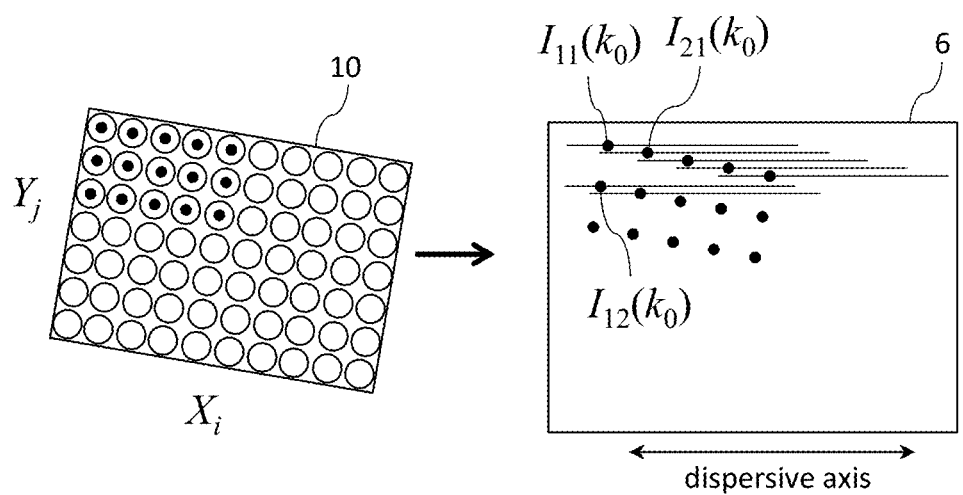
FIG. 7 illustrates the mapping of a 2-D grid of beamlets dispersed onto a 2-D sensor array.

From the combined interferogram measured by the 2-D sensor array 6 and knowledge of the wavelength mapping for each lenslet onto the 2-D sensor array we can extract a set of interferograms $I_{i,j}(k_l)$ where i, j denote the lenslet positions within the lenslet array 10 and $k_l$ denotes the wavenumbers resolved by the spectrometer (i.e. the grating) as illustrated in FIG. 7. It is convenient to consider the interferograms $I_{i,j}(k_l)$ as a sequence of two dimensional interferograms, one for each of M distinct wavenumbers. The dimension of each 2-D interferogram is equal to that of the lenslet array, for example 25 rows×40 columns. As such, the analysis is analogous to that of full-field swept source holoscopy (Hillmann et al, *Optics Express* 20(19), 21247-21263 (2012)), the key difference being that the low sampling resolution of the lenslet array compared to that of a photodetector array (e.g. 300 μm lenslet pitch compared to 5 μm pixels) limits the field of view achievable in a single snapshot. As the sample is measured in the Fourier plane, the image plane is obtained by applying a 2-D spatial Fourier transform to each interferogram. Advantageously, with an off-axis reference the Fourier transform can be used to separate positive and negative spatial frequency components of the interferogram, so that a subsequent 1-D FFT along the spectral axis of the positive spatial frequency component achieves full axial depth range. This can be readily seen from the lateral Fourier components of the cosine term in equation (1):

$$\delta\left(k_x \pm \frac{k(x' - x_0)}{f}\right)\delta\left(k_y \pm \frac{k(y' - y_0)}{f}\right)e^{\pm i2k\Delta z(x',y')} \quad (3)$$

The phase of the respective terms is now dependent on the sign of Δz.

We note that if the sample is on one side only of the zero delay, an off-axis reference is not required. The complex signal with unambiguous phase is obtained by a first 1-D FFT along the spectral axis, and then for positive delays, a subsequent spatial 2-D FFT. So for a given lateral bandwidth the lateral range is doubled compared to a full ranged system.

As an illustration of the field of view achievable with the Fourier plane sampling spectral OCT apparatus shown in FIG. 4 or 5, we consider the following set of parameters. The lenslet array 10 has pitch P=300 μm, NA=0.08, and spot size=0.61λ/NA=6.1 μm at wavelength λ=0.8 μm. For the objective lens 22 we assume f=40 mm and diameter D=11 mm (NA=0.14), giving an expected resolution of 3.6 μm. The maximum lateral range ($\Delta x=x-x_0$) for a full range system can be estimated from the Nyquist limit (λ·f)/Δx) >2P, which gives Δx<55 μm. The lateral range for cases in which delays are on one side only of the zero delay is twice this value, Δx<110 μm. Here we assume unit magnification between the objective lens 22 and the lenslet array 10, and note that a lateral field of 55 μm gives a change in the focal position of the lenslet array of <0.5 times the focal spot size of each lenslet.

Figure 8:
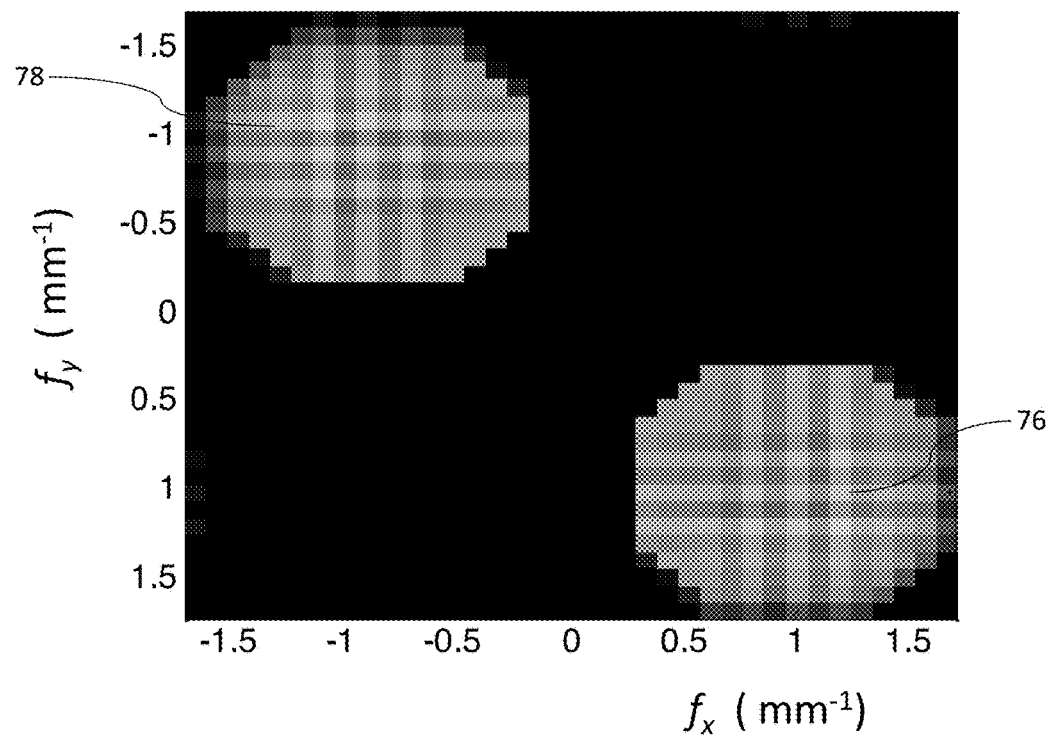
FIG. 8 shows the magnitude of an exemplary 2-D Fourier spatial transform of an interferogram obtained with sampling in the Fourier plane.

FIG. 8 illustrates the magnitude of the 2-D spatial Fourier transform of $I_{i,j}(k_l)$ for the above parameters, with the reference beam offset to ensure that the positive and negative frequency components 76, 78 are separated. In this particular example the reference beam is offset in both the horizontal and vertical axes, and we have subtracted out the non-interferometric terms. Either the positive frequency component 76 or the negative frequency component 78 can be extracted by filtering, and the frequency offset removed. From equation (3) we see that for a given sample position the spatial frequency is wavelength dependent. This wavelength dependence is removed by multiplication with a wavelength dependent phase factor prior to taking the Fourier transform over the spectral components, to obtain the full range depth profile.

In other embodiments the combined beams are sampled in the image plane. As illustrated schematically in FIG. 9, light 18 reflected or scattered from a point (x',y') in an illuminated volume 19 of a sample 20 is magnified and re-imaged onto a lenslet array 10. The complex field is obtained by mixing the returning sample light 18 with an off-axis reference beam 24 having an angle of incidence α. As in Fourier plane sampling, the focused beamlets 14 from the lenslet array are passed through an optional aperture array 25 then collimated, dispersed and focused onto a 2-D sensor array 6. In this case the reference beam 24 is required to be off-axis to separate the positive and negative frequency components of the signal. As explained previously, in preferred embodiments the lenslet array is rectilinear in configuration and tilted with respect to the dispersive axis of the dispersive element to provide a mapping of the dispersed beamlets onto unique sets of pixels 16-1, 16-2 etc of the sensor array 6. The complex field is obtained from a first spatial Fourier transform across the sampled field, setting negative frequency components to zero and then applying an inverse Fourier transform. As in the Fourier plane case a subsequent Fourier transform along the spectral axis 8 provides the full-range reflectivity profile of the illuminated volume 19 of the sample 20. A number of optical characteristics of the sample can be extracted with spatial resolution from this reflectivity profile, including for example phase, reflectivity, refractive index, refractive index changes and attenuation, as well as birefringence and degree of polarisation if the measurement system is polarisation sensitive.

Figure 10:
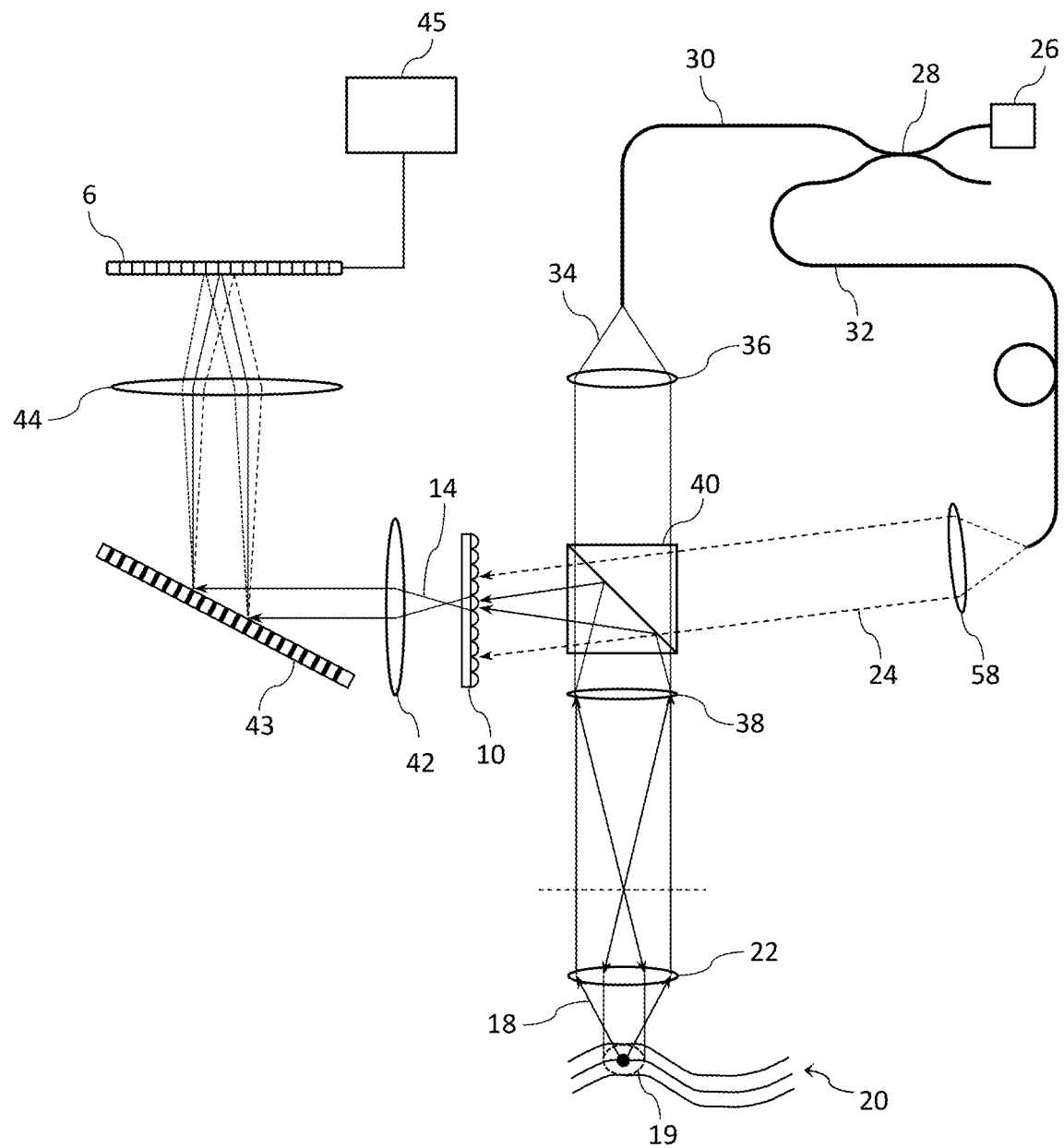
FIG. 10 illustrates a spectral domain OCT apparatus configured for image plane sampling of light scattered or reflected from a sample, according to an embodiment of the present invention.

FIG. 10 shows a spectral domain OCT apparatus configured for image plane sampling of light reflected or scattered from a sample 20, with high lateral resolution. In an illumination system of the apparatus, light from an optical fibre-coupled multi-wavelength or broadband source 26 is split with a 2×2 optical fibre coupler 28 into a sample arm 30 and a reference arm 32. As with the FIG. 4 apparatus the splitting ratio of the 2×2 coupler may for example be 90/10 or 99/1 sample/reference. The sample beam 34 is collimated with a lens 36 then directed onto an extended contiguous volume 19 of a sample 20 via a converging lens 38 and an objective 22. In preferred embodiments the objective has a relatively high numerical aperture to ensure high lateral spatial resolution. For example a 0.16 NA objective typically provides a spatial resolution of 3.0 µm.

In a measurement system of the apparatus, reflected or scattered sample light 18 from within the interaction volume 19 is collected with the objective 22 and directed to a beam splitter such as a beam-splitting cube 40 where it is mixed with an off-axis collimated reference beam 24. The combined beam is sampled in the image plane with an appropriately positioned 2-D rectilinear lenslet array 10, optionally followed by an aperture array (not shown), and each beamlet 14 is collimated with a lens 42, dispersed with a wavelength dispersive element in the form of a reflective grating 43, and focused via a lens 44 onto a 2-D sensor array 6, from which the combined interferogram can be read out in a single frame for subsequent analysis by a processor 45 equipped with suitable machine-readable program code. Alternatively, the dispersive element could be a transmissive grating or a prism. As described above in relation to FIG. 2, the lenslet array 10 is preferably tilted with respect to the dispersive axis of the grating 43 so that each beamlet 14 is mapped onto a unique set of pixels of the sensor array 6. In one particular embodiment the lenslet array has 1000 lenslets in a rectilinear 40×25 grid with a 300 µm pitch, and the 2-D sensor array is a 20 Megapixel CMOS camera with a pixel size of 5.5 µm. With this image plane sampling scheme, each beamlet 14 contains phase and amplitude information from a different portion of the interaction volume 19.

As before, the combined interferogram read out from the sensor array 6 represents a wavelength-dependent measurement of a signal of light reflected or scattered from the interaction volume 19, where the signal is a function of the phase and amplitude of the electric field vector of the reflected or scattered light 18. Using mathematical techniques described below, these wavelength-dependent measurements can be processed to generate numerical representations or construct a three-dimensional image of an optical characteristic of the sample with spatial resolution over at least a portion of the interaction volume. We note that the measurement system could be made polarisation sensitive, e.g. by inclusion of a polarisation walk-off element in front of the 2-D sensor array 6 as described below with reference to FIG. 14. In this case the optical characteristic could be related to a polarisation property of the sample, such as birefringence or degree of polarisation.

Figure 11:
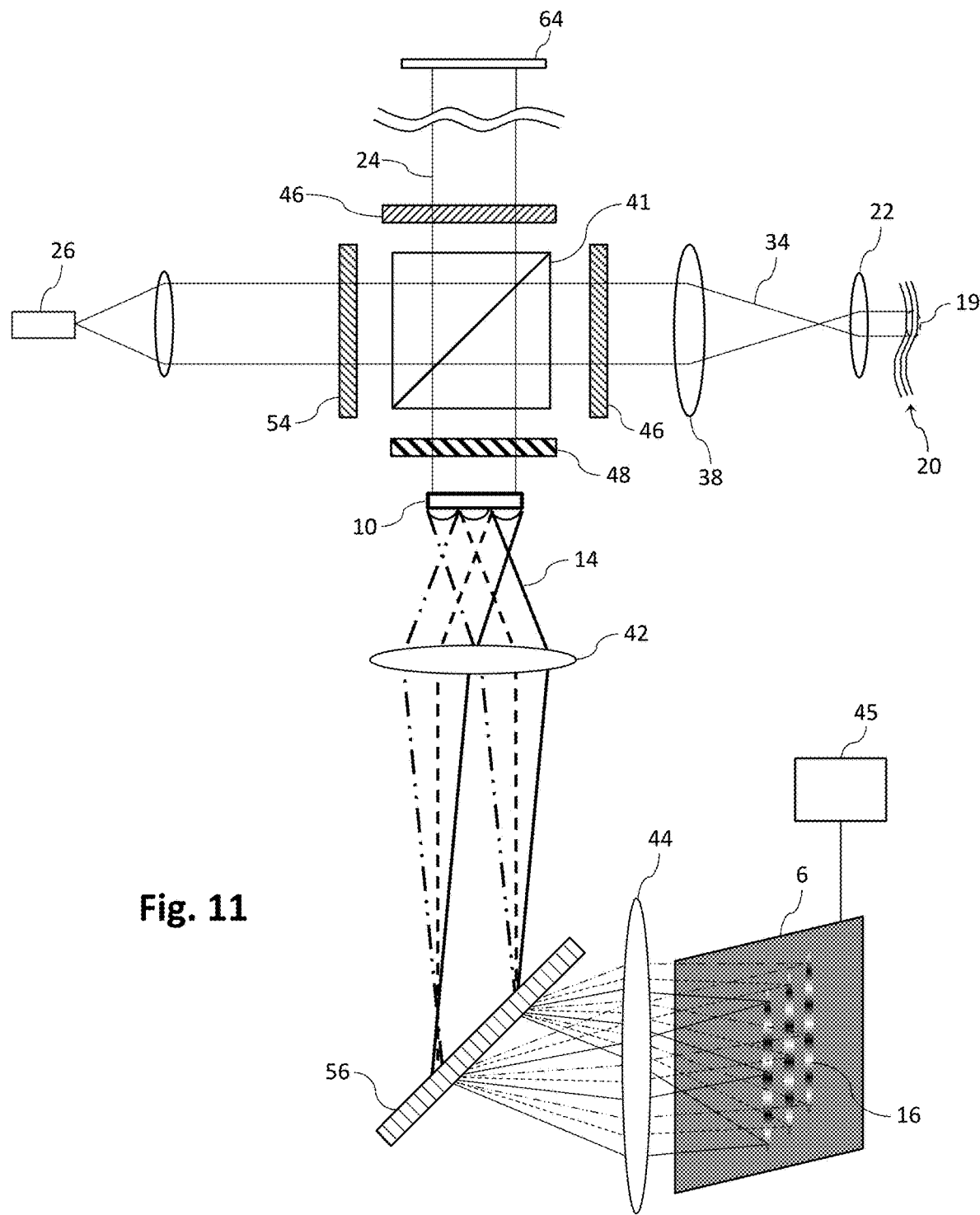
FIG. 11 illustrates another spectral domain OCT apparatus configured for image plane sampling of light scattered or reflected from a sample, according to an embodiment of the present invention.

FIG. 11 shows another spectral domain OCT apparatus configured for image plane sampling of light reflected or scattered from a sample 20, with high lateral resolution. In this apparatus the sample beam 34 and reference beam 24 are generated and combined with a polarisation beam splitter 41, quarter waveplates 46 and a polarisation analyser 48. As discussed above regarding FIG. 6, the polarisation analyser 48 can be oriented such that its transmission axis is close to parallel to the polarisation direction of the low intensity returning sample beam, to reduce the loss in sample power. Better equalisation of the reference and returning sample beam powers can also be achieved with an optional quarter waveplate 54 in the source arm, oriented such that the polarisation beam splitter 41 preferentially directs the light from the broadband source 26 into the sample arm.

A combination of a converging lens 38 and a high NA objective 22 is used to illuminate an extended contiguous volume 19 of a sample 20, for example 100 µm in lateral diameter, similar to the case with the apparatus shown in FIG. 10. Reflected or scattered sample light from within the illuminated volume 19 is collected with the objective 22 and mixed with the reference beam 24, noting that the reference mirror 64 is angled in the non-dispersive axis so that the reference beam is off-axis with respect to the returning sample beam. The combined beam is sampled in the image plane with an appropriately positioned 2-D rectilinear lenslet array 10, followed by an optional aperture array (not shown), and the resulting beamlets 14 collimated with a lens 42, dispersed with a wavelength dispersive element in the form of a transmissive grating 56, and focused via a lens 44 onto a 2-D sensor array 6. Alternatively, the dispersive element could be a reflective grating or a prism. As described above in relation to FIG. 2, the lenslet array 10 is preferably tilted with respect to the dispersive axis of the grating 56 so that each beamlet is mapped onto a unique set of pixels 16 of the sensor array 6. The combined interferogram can be read out from the 2-D sensor array in a single frame for subsequent analysis by a processor 45 equipped with suitable machine-readable program code. As with the FIG. 10 apparatus, each beamlet 14 contains phase and amplitude information from a different portion of the illuminated volume 19.

Figure 12:
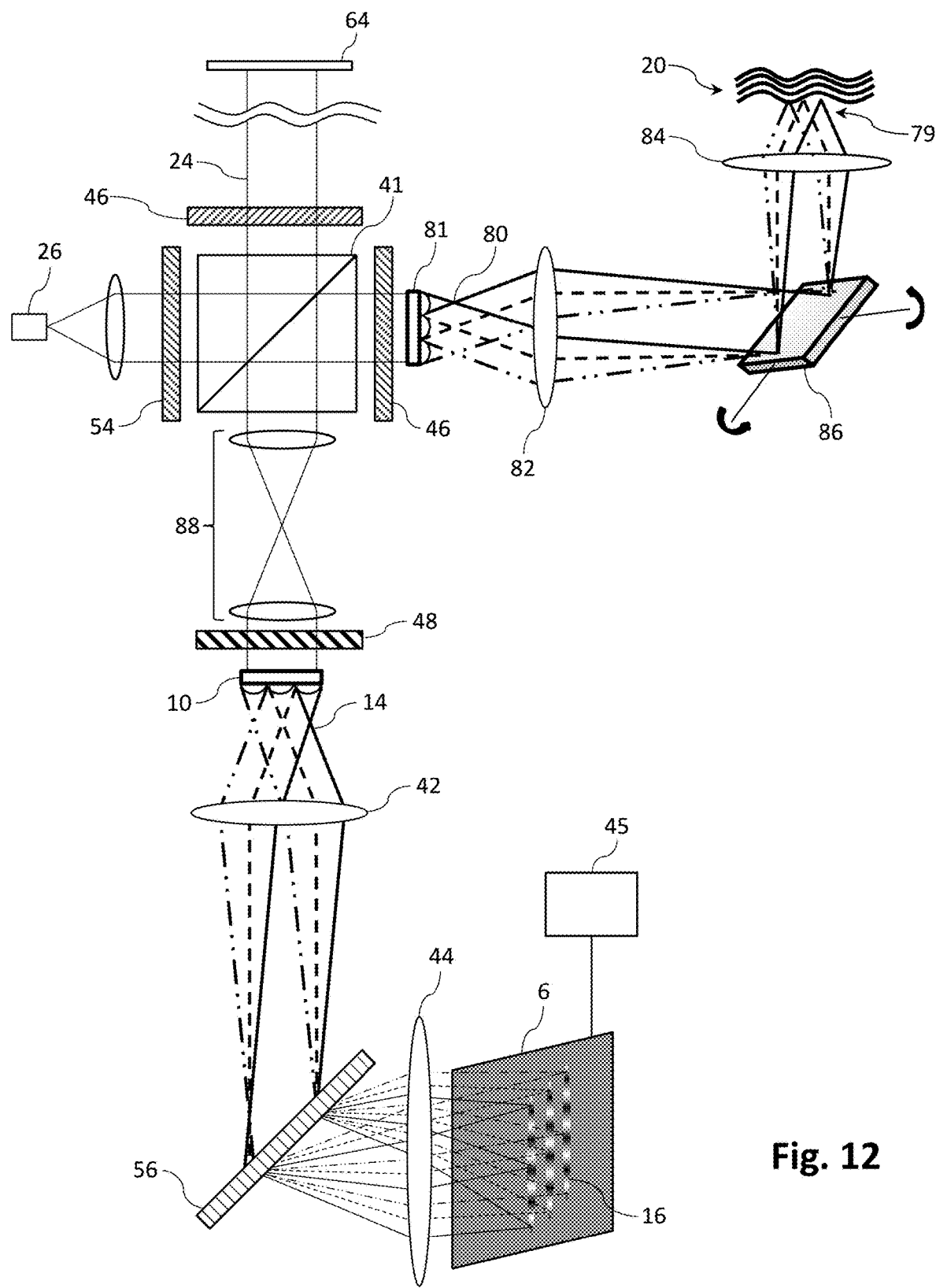
FIG. 12 illustrates yet another spectral domain OCT apparatus configured for image plane sampling of light scattered or reflected from a sample, according to an embodiment of the present invention.

FIG. 12 shows yet another spectral domain OCT apparatus configured for image plane sampling, in this case of light reflected or scattered from a 2-D grid of discrete spots 79 on a sample 20 rather than from an extended contiguous area. In an illumination system of this apparatus, a 2-D lenslet array 81 in the sample arm separates the sample beam into a grid of beamlets 80 that are focused onto the sample via lenses 82 and 84 and a mirror 86. Optionally this mirror can be scanned in one or two axes to translate the focused beamlets across the sample, e.g. to analyse different regions or fill in the gaps between the beamlets. Alternatively the sample 20 can be mounted on a translation stage. The lenses 82 and 84 generally form a high magnification system, e.g. 100×, and it may be preferable to include additional lenses to perform the magnification in two or more stages.

In a measurement system of the apparatus, sample light reflected or scattered from the discrete spots 79 is collimated by the sample arm lenslet array 81, relayed to the combined arm lenslet array 10 by means of a 4F lens system 88, and mixed with a reference beam 24 rendered off-axis by angling the reference mirror 64 in the non-dispersive axis. As in the FIG. 11 apparatus the combined beam passes through a polarisation analyser 48, then is sampled in the image plane with an appropriately positioned lenslet array 10 followed by an optional aperture array (not shown). The resulting beamlets 14 are collimated with a lens 42, dispersed with a wavelength dispersive element in the form of a transmissive grating 56, and focused via a lens 44 onto a 2-D sensor array 6 to form a combined interferogram. Alternatively, the dispersive element could be a reflective grating or a prism. The combined interferogram can then be read out from the 2-D sensor array in a single frame for subsequent analysis by a processor 45 equipped with suitable machine-readable program code. The combined interferogram represents a wavelength-dependent measurement of a signal of light reflected or scattered from the grid of discrete spots 79, where the signal is a function of the phase and amplitude of the electric field vector of the reflected or scattered light.

Scanning of the mirror 86 or translation of the sample 20, if enabled, can be controlled conveniently in synchronisation with read out of the sensor array by means of the processor 45 when equipped with suitable machine-readable program code.

Figure 9:
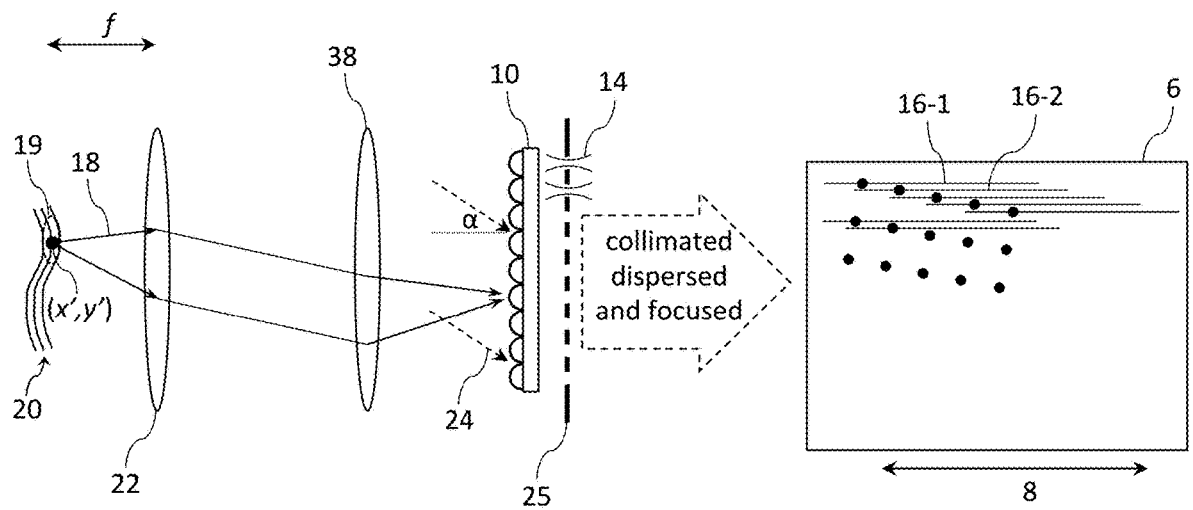
FIG. 9 illustrates an embodiment of the FIG. 2 scheme with sampling in the image plane.

We turn now to a description of an analysis of interferometric data obtained when sampling in the image plane light scattered or reflected from an extended contiguous volume 19 as shown in FIGS. 10 and 11. Assuming that the sample 20 is in a focal plane of the objective lens 22 as shown in FIG. 9, the interferometric signal component incident at position X, Y upon the lenslet array 10 can be expressed as:

$$I(X, Y, k) = S(k) R\left(\frac{X}{M}, \frac{Y}{M}\right)^{1/2} \cos(k(2\Delta z + Y\sin(\alpha))) \quad (4)$$

where M is the magnification of the lens system 22, 38 in the sample arm and α is the incident angle of the reference beam 24 at the lenslet array 10 as shown in FIG. 9. In this case the reference beam is assumed to be aligned with the Y-axis of the lenslet array. Importantly, for full range imaging a must be large enough to separate the positive and negative frequency components of the interferometric signal.

The analysis follows an analogous approach to that used in off-axis swept wavelength OCT, described for example in Huang et al, *Applied Optics* 52(5), 958-965 (2013), or in Fechtig et al, *Journal of Modern Optics* 2014 (DOI: 10.1080/09500340.2014.990938). The complex field is obtained by taking the Fourier transform along the Y axis, removing the negative frequency components and the frequency offset, and then applying an inverse Fourier transform to obtain the complex interferogram $I_{i,j}(k)$ where i, j denote a lenslet at position $(X_i, Y_j)$.

We assume similar experimental parameters to the previous far-field case, i.e. a resolution of 3.6 μm (objective NA=0.14), a transverse range of 55 μm and lenslet pitch P=300 μm. A large magnification between the sample and the lenslet array transforms the high numerical aperture high resolution sample information to a lower numerical aperture spot of dimensions comparable to the lenslets that can optimally interfere with the reference beam after they are both focused by the lenslet array. This range of incident angles is approximated by Δθ<λ/(2P) i.e. ~½ the Airy radius. A magnification of NA/Δθ≈100 will therefore ensure that rays emitted from the sample are captured. We note that this is equivalent to requiring the lenslet array pitch to be smaller than the magnified resolvable spot size.

In the above discussion it was assumed that the sample was in the focal plane of the objective lens. In general however, with three-dimensional samples the majority of the interaction volume will be somewhat displaced from the focal plane. Scattering from points away from the focal plane gives rise to curved wavefronts at the lenslet array. The capture of partially overlapping consecutive 3-D snapshot samples enables accurate phase registration of datasets, to which digital refocusing techniques can be applied using a processor equipped with suitable machine-readable program code, either before or after the snapshot samples are stitched together to form a 3-D composite image. Alternatively, digital refocusing can be applied directly to lateral points at the centre of the snapshot datasets, so as to avoid refocusing stitched datasets. Digital refocusing requires a first measurement of the signal with unambiguous phase and thus can be applied to both a full range system with an off-axis lateral reference and a system with all delays of the same sign and an on-axis lateral reference. The signal can be digitally refocused by adapting one of a number of well known techniques described for full field and line field systems, for example in Kumar et al, *Optics Express* 22(13), 16061-16078 (2014), or models such as that used in Fechtig et al, *Journal of Modern Optics* 2014 (DOI: 10.1080/09500340.2014.990938). Although these approaches are applied to OCT systems that sample the image plane, they can be adapted to sampling of the Fourier plane. The digital focusing technique described in Hillmann et al, *Optics Express* 20(19), 21247-21263 (2012) can be directly applied to the case in which we sample in the Fourier plane.

As an alternative embodiment to the various spectral domain OCT apparatus described previously, FIG. 13 shows a linear OCT apparatus configured for image plane sampling of light scattered or reflected from a sample. In an illumination system of the apparatus, light from a multi-wavelength or broadband optical source 26 is split with a beam splitter 40-1 to form a sample beam 34 and a reference beam 24. As in the apparatus shown in FIG. 10, an extended contiguous volume region 19 of a sample 20 is illuminated by a collimated sample beam 34. In a measurement system of the apparatus reflected or scattered light 18 is collected and magnified with a telescope system comprising lenses 22 and 38, and sampled in the image plane by an appropriately positioned rectilinear 2-D lenslet array 10 followed by an optional aperture array (not shown). The resulting beamlets 14 are then collimated with a lens 42 and directed onto a 2-D sensor array 6 via another beam splitter 40-2. In contrast to the previously described spectral domain approach, a collimated reference beam 24 is dispersed, e.g. with a reflective grating 43, then mixed with the sample field directly onto the sensor array 6. The rectilinear lenslet array 10 is preferably tilted with respect to the dispersive axis of the grating 43 so that the wavelength-dependent spatial frequency components obtained from a 2-D FFT for each beamlet 14 are mapped onto a unique set of pixels of the 2-D sensor array 6. These wavelength-dependent spatial frequency components can be read out from the 2-D sensor array for subsequent analysis by a processor 45 equipped with suitable machine-readable program code. Each component represents a wavelength-dependent measurement of a signal of light reflected or scattered from a different portion of the interaction volume 19, where the signal is a function of the phase and amplitude of the electric field vector of the reflected or scattered light 18.

For a given wavelength, a 2-D FFT 134 of the corresponding interferogram read out from the sensor array 6 is illustrated in FIG. 13A. Each beamlet corresponding to a lenslet in the lenslet array 10 is represented by a distinct spatial frequency component 136 with both amplitude and phase. The dispersive grating 43 in the reference arm enables the amplitude and phase of each wavelength component of each beamlet to be measured. Because the lenslet array 10 is angled with respect to the dispersive axis of the grating 43 the spectral content of the beamlets remain distinct in the frequency domain, allowing us to obtain a distinct 2D-FFT 138 for each beamlet as shown in FIG. 13B. A 1-D Fourier transform over the spectral component of the positive spatial frequency content provides the full range 3-D depth profile. For simplicity the dispersed beamlets 140 are depicted in FIG. 13B as being parallel, although in practice their slopes will generally vary with the incident angle of the beamlets 14 onto the sensor array 6 and hence will not be identically parallel. Nevertheless, with appropriate system design the variations in slope between the dispersed beamlets 140 will be sufficiently small such that they do not overlap in spectral content.

An advantage of this approach compared to the spectral domain OCT approach is that it potentially avoids an expensive and difficult to align spectrometer. As with the spectral domain approach, a reference beam tilted in the axis perpendicular to the dispersive axis allows the positive and negative frequency terms 142 and 144 to be separated, as seen in FIG. 13A. Consequently the 1-D FFT along the spectral axis enables a full-range axial measurement. Similarly, in analogy with the spectral domain approach, digital wavefront correction and measurement can be implemented. Linear OCT however suffers from the well-known time domain sensitivity penalty compared with spectral domain OCT. For applications in which a comb of discrete wavelengths can be used, i.e. sparse axial reflectivity profiles, this sensitivity penalty can be reduced.

As mentioned previously, there is a trade-off in OCT imaging between transverse resolution and depth of field. Fundamentally, this trade-off arises because higher NA lenses enable smaller spot sizes, and therefore increased transverse resolution, but at the cost of reduced depth of field.

Figure 14A:
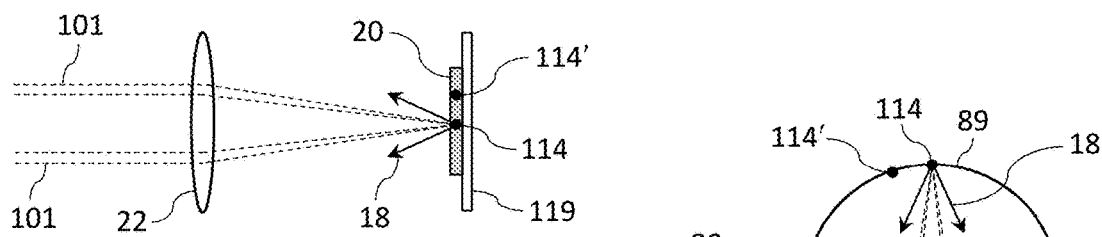
FIG. 14A shows in inset form a variation on the FIG. 14 apparatus, for providing angularly structured illumination to a non-ocular sample.
Figure 14:
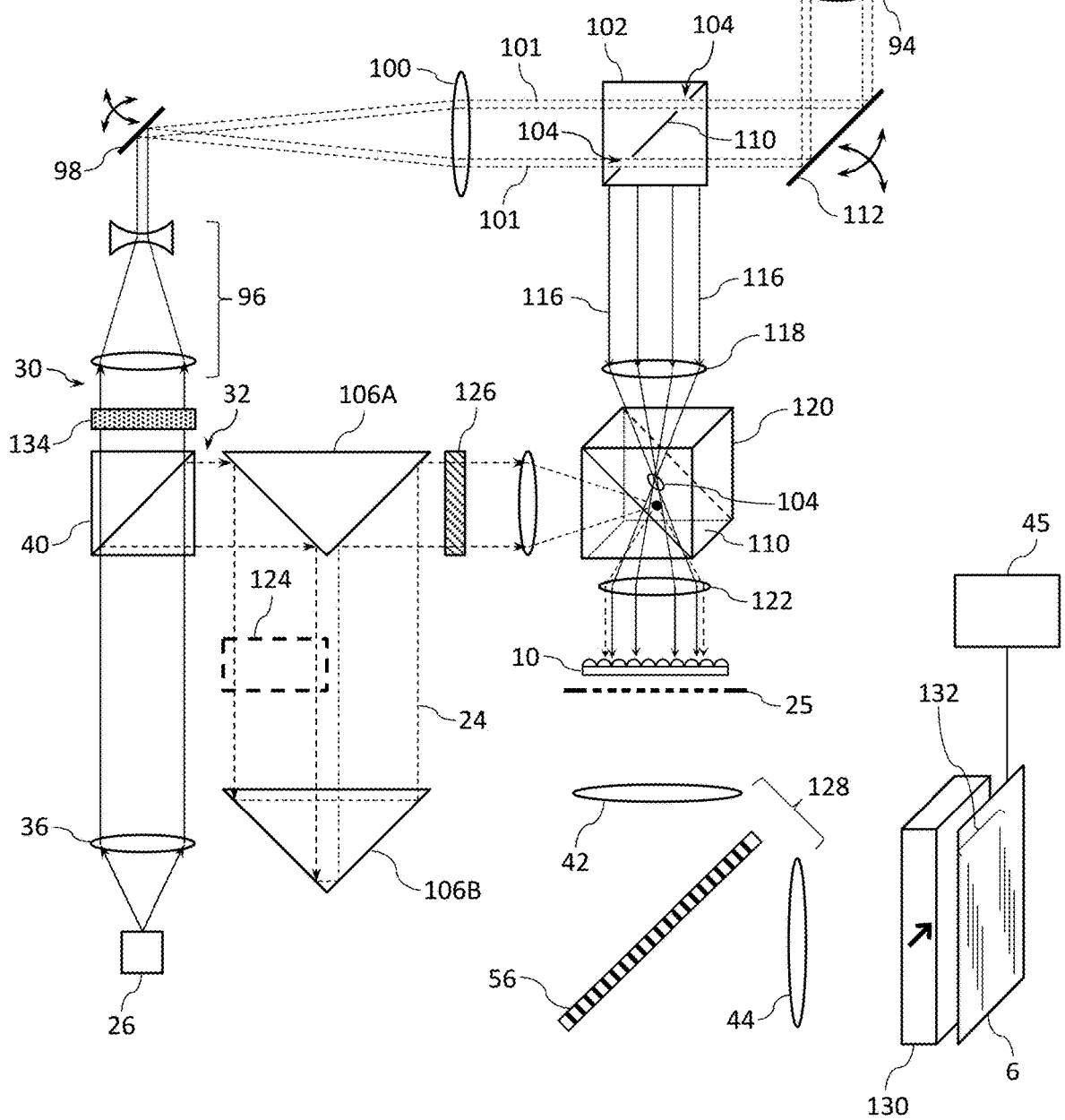
FIG. 14 illustrates a spectral domain OCT apparatus suitable for providing angularly structured illumination to an ocular sample for enhanced lateral resolution and/or extended depth of focus, according to an embodiment of the present invention.

FIG. 14 shows an apparatus for retinal imaging, in which the retina 89 of an eye 90 is illuminated at a number of different angles through a lensing system with a limited numerical aperture. For ocular samples the numerical aperture is limited by the size of the pupil 92, while in other microscopic optical systems or for other samples the numerical aperture of the imaging system may be limited by the size of the optical elements. Importantly, the angularly structured illumination provided by this apparatus, i.e. the illumination of a volume 114 of the retina at two or more incident angles, enables higher lateral resolution than would otherwise be possible with an imaging system of limited numerical aperture, while retaining the increased depth of field advantage of lower numerical aperture. Note that this angularly structured illumination is distinct from the different angles incident onto the cornea 94, controlled by the mirror 112, required to illuminate different volumes of the retina 89 as explained below.

Light from a superluminescent light emitting diode (SLED) 26 or some other broadband or multi-wavelength source is used both to probe the retina 89 and to measure interferometrically properties of the retina via reflected or scattered light. In most general form, the light source 26 should emit light having at least first and second wavelengths. When using polarisation-sensitive detection as described below, the light source should be polarised, i.e. emits light of a given polarisation state. In an illumination system of the apparatus, the SLED output is formed into a beam by a collimating element 36 and split into a sample path 30 and a reference path 32 by a polarisation-insensitive beam splitting element 40 such as a conventional polarisation independent beam-splitting cube as used for example in the FIG. 4 apparatus. The sample path beam is reduced in size with a beam reducer 96 such as a reversed Gaussian beam expander and directed to a beam steering element 98 such as a two-axis MEMS mirror. This beam steering element is adapted to direct the sample path beam in a number of paths that become parallel and spatially separated after traversing a parallelising element 100. In the illustrated embodiment this parallelising element is a lens positioned one focal length away from the MEMS mirror 98, although in other embodiments it could be a prism or a mirror. In certain embodiments the parallelising element also resizes the sample beam. Each resultant beamlet 101 should be significantly smaller in diameter than the pupil 92 of the sample eye, so that it will illuminate a small area of the retina 89, preferably with a diameter in the range of 50 to 500 μm in the present case. For a normal relaxed eye a parallel set of beamlets 101 will come to illuminate the same point of the retina, though for a highly myopic eye it may be necessary to adjust the position of the parallelising element 100 to provide a non-parallel set of beamlets that will largely overlap at the retina. In an alternative embodiment the beamlets 101 are generated simultaneously with a diffractive optical element (DOE) instead of sequentially with the MEMS mirror 98, in which case the illumination onto the retina will be in the form of a simultaneous angularly structured illumination. Generally speaking the sequential embodiment is more straightforward analytically, so long as the analysis is not unduly influenced by sample movement between frames.

Figure 15:
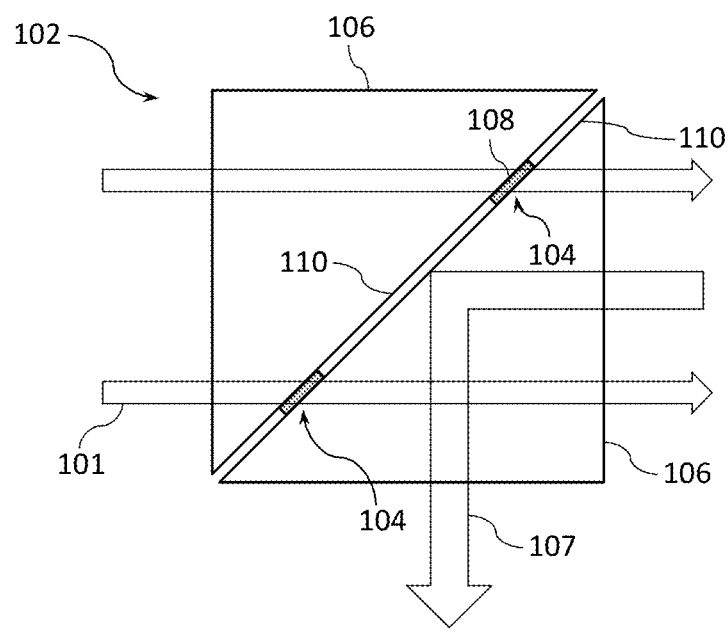
FIG. 15 shows an apertured reflector suitable for use in the apparatus of FIG. 14.

The sequence or simultaneous array of beamlets 101 is passed through a beam splitting element, which in preferred embodiments comprises an apertured reflector 102, wherein they are able to pass through a number of discrete apertures 104 without significant loss, at positions that can be addressed by different angles of the MEMS mirror 98 (for sequential beamlets) or the structure of a DOE (for simultaneous beamlets). In general form the apertured reflector has a surface, preferably a total internal reflection surface 110, for reflecting light, and one or more apertures 104 that locally disrupt the total internal reflection at that surface, for transmitting light without reflection. In one embodiment the apertured reflector comprises a prism with a polished optical surface for total internal reflection, and one or more apertures in the form of drilled holes that disrupt the total internal reflection. In a preferred embodiment illustrated in FIG. 15 the apertured reflector 102 comprises a pair of prisms 106 that provide total internal reflection 107 at one or other of the polished optical surfaces 110 except in the apertures 104 defined by droplets 108 of an index matched adhesive that fixedly attach and space apart the reflective surfaces. The separation between the prisms 106 imparted by the droplets of adhesive is not a critical parameter, but may for example be in the range of 5 to 500 μm, e.g. approximately 10 μm. Preferably the prisms 106 are right angle prisms as shown. The choice of an apertured beam splitting element 102 may be particularly advantageous over a conventional power beam splitter as it enables the illumination of a sample and capture of back-reflected light independent of polarisation and with low intrinsic power losses. Obviously some signal light will be lost through the apertures 104 in the return path, but this can be minimal when the illuminating beamlets 101 are small because the overall area of each reflective surface 110 is significantly larger than the apertures 104. The beam splitting element 102, in whatever form, is preferably polarisation independent, and any residual polarisation sensitivity can be calibrated out if necessary.

Returning to FIG. 14, the beamlets passing through the apertured reflector 102 are then incident onto an angularly variable element in the form of a steerable mirror 112, optionally in combination with an optical relay system (not shown), which directs them onto a common interaction volume 114 of the retina 89. It will be appreciated that the beamlets 101 are directed onto the common interaction volume 114 at different incident angles, determined by the beam steering element 98 and the optical power of the eye 90. The position of the common interaction volume 114 on the retina can be varied, e.g. to position 114', by angular adjustment of the mirror 112 so that a larger area of the retina can be imaged via collection of a number of images that can be stitched together to create a composite image. Light 18 scattered or reflected from the interaction volume 114 for a given position of the mirror 112 is then captured across the whole pupil 92, collimated roughly by the eye's optical power then directed by the mirror 112 to have an equivalent propagation direction independent of the point of illumination of the retina for the case of an ideal relaxed eye focused at infinity. After being directed away from the optical source 26 by the apertured reflector 102, the roughly collimated return beams 116 are focused down by a lens 118 to form an image of the retina. Preferably the lens 118 is of variable focus to provide some gross aberration correction to adapt for the large variations of myopia and astigmatism typically found in a clinical setting. Variable focus lenses are provided for example by Varioptic.

We note that the apparatus shown in FIG. 14, unlike the FIG. 4 apparatus for example, does not require an objective lens 22 to illuminate the common interaction volume 114 and collect the scattered or reflected light 18, because these functions are performed by the cornea and lens of the sample eye 90. As illustrated in FIG. 14A, the sample-related portion of the FIG. 14 apparatus can be adapted for providing angularly structured illumination to other types of sample 20 by the inclusion of an objective lens 22 or other optical power element, with the sample located at or close to a focal plane of this lens. The objective lens directs the beamlets 101 onto a common interaction volume 114 of the sample 20, and collects the scattered or reflected light 18. In place of the angularly variable mirror 112, an X, Y translation stage 119 can be used to move the sample for imaging further volumes 114'. It will be appreciated that there are many other schemes for providing angularly structured illumination to one or more volumes of a non-ocular sample and collecting the scattered or reflected signal light, involving for example back illumination, beam splitters or combiners, and rotation of the sample.

The image of the retina is passed through a beam combiner 120 into a measurement system of the apparatus, which includes an interferometer. In the illustrated embodiment the beam combiner 120 is an apertured reflector similar to the element 102, but with a single aperture 104 for passing the image of the retina. This allows the returning sample beam to be combined with the reference beam 24 and sampled in the Fourier plane with an appropriately positioned 2-D lenslet array 10.

We turn now to description of the path of the reference beam 24, which is reflected at the beam splitter 40 and passed through a delay line comprising a pair of right angle prisms 106A, 106B that approximately maps the group delay of the sample arm light travelling to and from the sample eye 90. This delay line may incorporate a dispersion equalisation element 124 to ensure that dispersion in the reference arm 32 is similar to that in the sample arm 30. Optionally, the reference arm can include a polarisation modifying element 126 such as a half wave plate or a polariser to create a given polarisation state for the reference beam. Following the delay line, the reference beam 24 is focused onto a total internal reflection surface 110 of the apertured reflector 120 to form a focal point near to the position of the image of the retina (i.e. near to the aperture 104). The reflected reference beam and the transmitted sample beam are then approximately collimated by a lens 122 that converts the far field angular distribution into a spatial distribution, which can be sampled over a plane 2-D surface with a lenslet array 10. A co-registered aperture array 25 is preferably included to reject stray light that would compromise the resolution of the 2-D dispersive optical system 128 described below.

The use of an apertured reflector for the beam combiner 120 is particularly advantageous in this configuration as both the sample and reference beams, being focused at the beam combiner 120, can be passed into the interferometer portion of the apparatus without significant loss. If the lateral displacement between the sample and reference focal points is small then the impact of the offset on the fringe contrast in the interferometer can be minimised. Consequently the apparatus is able to provide a very high signal to noise ratio for a given illumination power on the sample, which obviously must be limited for ocular samples.

The 2-D dispersive optical system 128 comprises a first collimating lens 42 positioned about one focal length away from the aperture array 25, a wavelength dispersive element in the form of a transmissive grating 56 providing dispersion along one axis, and a second lens 44 for focusing the dispersed array of grid points onto a 2-D sensor array 6 such as a CMOS camera or other focal plane array. In alternative embodiments the dispersive element could be a reflective grating or a prism. Note that for simplicity of illustration, representative ray paths through the dispersive engine 128 are not shown in FIG. 14. As before, the orientations of the lenslet array 10 and the dispersive axis of the grating 56 are chosen so that the spectral dispersive lines created from each of the beamlets emerging from the apertures are slightly offset laterally as shown in FIG. 2. A polarisation walk-off element 130 such as a $YVO_4$ plate is provided to split the polarisation state of both the signal and reference beamlets, providing two wavelength-dispersed lines 132 for each sampling point (aperture or lenslet) as shown. In alternative embodiments without polarisation-sensitive detection the walk-off element 130 is omitted.

The operation of the imaging apparatus shown in FIG. 14 is firstly described for its normal lateral resolution mode, i.e. without angularly structured illumination, which is limited by the NA of the sample eye 90. During a single frame acquisition period of the CMOS camera 6, preferably operated in global shutter mode, the SLED 26 is pulsed for a period of time short enough to avoid significant motion artefacts in the eye. The sample beam is directed through a single aperture 104 of the apertured reflector 102 to illuminate a volume 114 of the retina 89 through a specific region of the pupil 92. The dispersed interferometric image of the back-reflected or scattered light from the illuminated volume, with or without the polarisation splitting conferred by the walk-off element 130, is then read digitally from the CMOS camera 6 and processed with a processor 45 equipped with suitable machine readable program code to provide a pixel-to-wavelength map for each of the sampling points defined by the lenslet array 10. The wavelengths can be converted into a linearised k-vector through interpolation as is well understood in the field of spectral domain OCT to construct a phase and amplitude map across the surface of the illuminated volume 114 for a regularly spaced set of k-vectors. As the set of sample points corresponds to a sampling of the electric field vector in the Fourier plane it is possible to use a Fourier transform to construct or generate a 3-D image or representation of the illuminated sample volume 114. Use of digital aberration correction and/or digital refocusing may be applied to maintain the lateral resolution of the image across an enhanced depth of field, compared to that which could be achieved in the case of a single scanning beam with an equivalent numerical aperture limitation.

The 3-D image or representation constructed or generated may be of a single polarisation amplitude or phase measurement of the reflected or scattered light, suitable for extraction of an optical characteristic of the sample such as phase, reflectivity, refractive index, refractive index changes or attenuation. Alternatively, if the detection system is polarisation-sensitive e.g. by virtue of a polarisation walk-off element 130, the image or representation may be of a polarisation property of the sample, such as birefringence or degree of polarisation, which may be indicative of the type of material being sampled. These measurement techniques are well understood for OCT systems (e.g. scanning, time domain or full field OCT systems) and can now be applied in a straightforward fashion.

In preferred embodiments the polarisation-sensitive detection system is complemented with a polarisation control element 134 such as a voltage-controlled liquid crystal element in the sample arm, to enable illumination of the sample volume 114 with light of a second, different polarisation state. In this case the measurement system makes a second, additional set of simultaneous measurements of the reflected or scattered light 18, and the processor 45 processes both sets of measurements to construct or generate a three-dimensional image or representation of one or more polarisation properties of the sample. This modification to the apparatus avoids, for example, the situation of being unable to measure sample birefringence if it happens to be parallel to an input polarisation state. In general, while illumination with a single polarisation and subsequent polarisation-sensitive detection can often provide a clinically useful contrast mechanism, the ability to make two or more separate measurements of a sample with differently polarised illumination states allows one to obtain a more complete description or representation of the polarisation properties of the sample.

To image an additional portion of the retina 89 the angular position of the mirror 112 is adjusted to illuminate a second volume 114', which is preferably adjacent to the first volume 114 and with a small overlap to facilitate registration of the composite stitched image. The process can be repeated for a number of angles of the mirror 112 to construct a three-dimensional composite image of an increasingly large area of the retina. Each of the individual images can be thought of as a numerical representation of an optical characteristic of the retina over the respective volume. Of particular interest is the fact that digital refocusing and/or aberration correction can be carried out for each of the individual volume images so that off-axis aberrations or changes in eye length as a function of retinal position can be post-processed after acquisition to provide a sharper image over the entire field of view. Alternatively digital refocusing and/or aberration correction can be applied after the individual volume images have been stitched together to form a single numerical representation of an optical characteristic of the retina over the combined volume. Variations in apparent eye length are a common feature with myopic patients for example, which would normally limit the resolution of the image without adaptive optics that can track the acquisition. This information about the level of digital refocusing for off-axis aberration could also be clinically meaningful in assessment of myopia progression, as it provides a quantitative measure of some of the axial aberrations of the eye under test. In visualising the layers of the retina or cornea, or of a non-ocular sample, it is often useful to do so as a B-scan wherein a slice of the sample is imaged. To enable this visualisation of high resolution detail in a B-scan, multiple adjoining volumes can be processed together encompassing the slice of interest, and the resulting three-dimensional composite image reduced to a high resolution B scan either through sampling or a weighted averaging of the area around the slice.

It will be appreciated that various elements in the FIG. 14 apparatus should be operated in a coordinated fashion. These include for example the SLED 26, the sample arm polarisation control element 134, the beam steering element 98, the angularly variable mirror 112 (or the translation stage 119) and the CMOS camera 6. This overall level of control may be provided, for example, by the processor 45 when equipped with suitable machine-readable program code.

To enhance the lateral resolution and depth of field achievable with an imaging system of given numerical aperture we now consider the case where for each set angle of the mirror 112 we take two or more measurements of the same volume 114 of the retina 89, illuminated in each case with a different incident angle via different paths through the pupil 92 and an aperture 104 in the apertured reflector 102. In one particular example the apertured reflector has four apertures, with two of the apertures separated at the extremes of the pupil in the vertical axis and the other two apertures separated in the horizontal axis. In certain embodiments the different illumination trajectories are established by angular adjustment of a 2-axis MEMS mirror 98 so the sample beam propagates sequentially through the specified apertures. In other embodiments the different illumination trajectories are established simultaneously, e.g. with a diffractive optical element (DOE) as explained previously. In the former case the multiple measurements of the volume 114 are taken sequentially, i.e. single shot acquisition for each illumination trajectory (incident angle). In the latter case the multiple measurements are taken simultaneously, i.e. single shot acquisition for all illumination trajectories. Either way, the far field captured for each of the different illumination trajectories therefore corresponds to angular offsets in the far field. In this manner, different regions of high frequency spatial content of the image, which would otherwise fall outside the NA of the system, have their frequency content shifted or 'mixed' down to baseband. Since each illumination trajectory captures a different high frequency region, the combined spatial content is potentially doubled compared with a single illumination capture, thereby achieving a super resolution of half the Rayleigh criterion. This approach is an improvement over Fourier ptychography, described for example in Dong et al 'Aperture-scanning Fourier ptychography for 3D refocusing and super-resolution macroscopic imaging', *Optics Express* 22(11), 13586-13599 (2014), in that the field is now captured interferometrically in a single snapshot rather than having to be iteratively reconstructed to be consistent with the intensity image. With our approach the passband of the Fourier field can be extended by registering and stitching together the different partial far fields to create a stitched Fourier Plane, with each partial far field acquired in a single shot. Fourier transformation or other digital processing of the extended Fourier field measurements results in an enhanced lateral resolution. We do not have to rely on iterative methods to infer what the field should have been based on intensity-only measurements.

There are many situations where Doppler-like measurements of relative phase are of value, e.g. for measuring capillary blood flow or for performing strain or elastography measurements in the presence of a mechanical, acoustic thermo-acoustic or ultrasound perturbations. To this end, the apparatus shown in FIG. 4 or FIG. 10 for example can be adapted to provide a relative phase-sensitive OCT apparatus that can be utilised for Doppler-like measurements of motion or distortion, and related quantities such as strain, over a 3-D volume of a sample. It will be appreciated that other previously described apparatus can be adapted in similar fashion.

In this 'Doppler' embodiment the multi-wavelength optical source 26 is triggered to produce at least first and second optical pulses, each with a duration sufficiently short to allow a phase measurement to be made in the presence of the motion or distortion which is to be measured within the interaction volume 19. The reflected or scattered light 18 from the first pulse is captured and analysed in a single exposure or frame of the 2-D sensor array 6 as has been described earlier. After a predetermined time period a second pulse is generated and its reflected or scattered light 18 subsequently analysed in a second exposure of the 2-D sensor array. Each exposure, after read-out and analysis, provides a complex image comprising phase and amplitude information from the interaction volume over a range of wavelengths. In certain embodiments the timing between the pulses is less than the frame rate of the sensor array, which can be achieved by appropriately timing the pulsed illumination with respect to the exposures of the sensor array. That is, a first pulse can occur near the end of one frame, and a second pulse near the beginning of the next frame. Obviously the pulsing of the optical source 26 needs to be coordinated with operation of the sensor array 6. In certain embodiments the optical source 26 is triggered by the same processor 45 that reads out and analyses data from the sensor array.

When using far field or Fourier plane sampling as shown in FIG. 4, the sample reflection spectra are analysed in the Fourier plane over an array of locations corresponding to the sampling of the 2-D lenslet array 10. It is worth noting that for a given depth (corresponding to a frequency component of the spectral interferogram) within the interaction volume 19 located approximately at the focal plane of the lens 22 there is, for each lateral sample location, a 2-D far field spatial frequency component. Furthermore a given specular reflection or speckle frequency component will have a phase associated with it. The lateral phase of a specific reflection is detected on the 2-D sensor array 6 and can be retrieved during the numerical processing by the processor 45 by a complex FFT that returns both phase and amplitude of reflection with spatial resolution, i.e. a complex image, over the interaction volume 19. In regions where the amplitude is sufficiently strong to provide a meaningful phase measurement, a set of points can be established over which the phase can be mapped. In certain embodiments the mapping constitutes just the axial component of the phase, obtained by the FFT of the spectral components. In other embodiments the mapping also comprises the transverse phase components, corresponding to the phase of the spatial far field components. The transverse phases need to be scaled according to the focal length of the lens 22, and will typically be a less sensitive measure of displacement. That is, a given phase shift would represent a larger displacement than the axial phase shift by a factor of around 3 to 10, depending on the numerical aperture of the captured light 18. Even allowing for the reduced sensitivity, for submicron displacements, this is still a valuable measurement that would be difficult to achieve accurately using a conventional raster-scanning OCT system. It can therefore enable a more accurate measurement of the true velocity vector, i.e. rate of displacement, especially for cases where a capillary flow or other motion to be measured is largely in the transverse plane and hence lacking an axial component.

If there is no bulk motion or distortion of the sample 20 between the illumination pulses, i.e. coarse movement much larger than the intra-sample motion or distortion of interest in the Doppler measurement, it is straightforward simply to subtract the relative phases of the data sets of points. However this is not always the case. It is particularly important for many measurements to be able to register adequately the two frames of information corresponding to the two measurement sets. This bulk registration between the frames can be achieved by optimising a cross correlation function in the presence of a grid transformation that provides a given displacement and distortion (e.g. linear compression) mapping of the grid of the sample between one frame and the next. Accurate registration of the two frames involves accounting for the phase shift associated with the mapping, to identify a basis from which to determine a relative phase shift caused by a displacement associated with intra-sample motion (e.g. capillary flow) or distortion (e.g. mechanical perturbation) that is being determined. Knowledge of the predetermined time period between the frames enables the rate of displacement to be determined.

Elastography determines the local elasticity or stiffness of a sample, such as biological tissue, from displacement measurements. Local displacements, induced for example by compression of the sample, may be accurately determined from relative phase measurements before and after compression. The local elasticity is inferred from the measured displacement as a function of depth. Alternatively, elasticity can be determined by using pulsed perturbations to generate low amplitude shear waves, with the velocity and dispersion of these waves being sensitive to the mechanical properties of the sample. Measuring the low amplitude sample displacements caused by the wave propagation requires the resolution offered by phase sensitive measurements.

It will be appreciated that the illustrated spectral domain OCT and linear OCT embodiments, in which returning sample and reference beams are sampled with a rectilinear 2-D lenslet array angled with respect to the dispersive axis of a wavelength dispersive element, enable single shot acquisition of 3-D images of a sample. In particular, the illustrated embodiments provide apparatus and methods for obtaining improved high resolution optical images of a retina based on numerical reconstruction of the spectral characteristics of light reflected from a small volume of the retina, with correction of aberrations present in the sample eye.

In each of the illustrated embodiments, focusing of light beams is performed with optical power elements in the form of lenses. However it will be appreciated that other forms of optical power elements such as off-axis parabolic or ellipsoidal mirrors could be used.

Although the invention has been described with reference to specific examples, it will be appreciated by those skilled in the art that the invention may be embodied in many other forms.

The claims defining the invention are as follows:

1. A high resolution optical imaging apparatus, comprising:
   (i) an illumination system for illuminating, with a multi-wavelength optical beam, a volume of a sample to be imaged in three spatial dimensions;
   (ii) a sampling system for sampling, at a two-dimensional grid of sampling points, light reflected or scattered from the illuminated volume of said sample;
   (iii) a measurement system for simultaneous capture of phase and amplitude information over a range of wavelengths of the sampled reflected or scattered light, over said two-dimensional grid of sampling points; and (iv) a processor for processing the phase and amplitude information to construct, using digital refocusing, a three-dimensional image of an optical characteristic of said sample over said illuminated volume, wherein said optical characteristic is selected from the group consisting of phase, reflectivity, refractive index, refractive index changes and attenuation, and wherein said apparatus is adapted to:

construct, from first and second measurements of said phase and amplitude information captured in single exposures a predetermined time period apart, first and second images of said optical characteristic;

register said first image to said second image to determine a spatially resolved phase shift caused by motion or distortion of said sample in any spatial dimension; and determine from said phase shift at least a component of the displacement of said sample associated with said motion or distortion.

2. The apparatus according to claim 1, wherein said processor is adapted to determine from said phase shift and said predetermined time period a rate of displacement of said sample associated with said motion or distortion.

3. The apparatus according to claim 1, wherein said processor is adapted to measure strain associated with said distortion of said sample.

4. The apparatus according to claim 1, wherein said processor is adapted to perform elastography measurements on said sample.

5. An article of manufacture comprising a computer usable medium having a computer readable program code configured to operate the apparatus according to claim 1.

6. A high resolution optical imaging apparatus, comprising:

an illumination system for illuminating, with a multi-wavelength optical beam, a volume of a sample to be imaged in three spatial dimensions;

(ii) a sampling system for sampling, at a two-dimensional grid of sampling points, light reflected or scattered from the illuminated volume of said sample;

(iii) a measurement system for simultaneous capture of phase and amplitude information over a range of wavelengths of the sampled reflected or scattered light, over said two-dimensional grid of sampling points; and (iv) a processor for processing the phase and amplitude information to construct, using digital refocusing, a three-dimensional image of an optical characteristic of said sample over said illuminated volume, wherein said optical characteristic is selected from the group consisting of phase, reflectivity, refractive index, refractive index changes and attenuation, and wherein:

said illumination system comprises a multi-wavelength optical source for illuminating said volume with light of at least a first polarisation state;

said measurement system is adapted to capture a first set of simultaneous measurements of said phase and amplitude information over a range of wavelengths, for at least first and second polarisation states; and said processor is adapted to process said phase and amplitude information to generate a three-dimensional representation of one or more polarisation properties of the illuminated volume of said sample.

7. The apparatus according to claim 6, wherein said one or more polarisation properties comprises birefringence or degree of polarisation.

8. The apparatus according to claim 6, wherein said illumination system is adapted to subsequently illuminate said volume with light of a second polarisation state, different from said first polarisation state, and said measurement system is adapted to capture a second set of simultaneous measurements of phase and amplitude information over a range of wavelengths.

9. The apparatus according to claim 8, wherein said processor is adapted to process the first and second sets of simultaneous measurements to generate a three-dimensional representation of one or more polarisation properties of the illuminated volume of said sample.

10. The apparatus according to claim 6, wherein said apparatus further comprises an optical splitter for directing a portion of light reflected or scattered from said sample away from said optical source.

11. The apparatus according to claim 10, wherein said optical splitter comprises a polarisation independent beam splitter.

12. The apparatus according to claim 10, wherein said optical splitter comprises an apertured reflector having a total internal reflection surface and one or more apertures that locally disrupt the total internal reflection at said surface, for allowing transmission of light for illuminating said sample.

13. The apparatus according to claim 12, wherein said apertured reflector comprises two total internal reflection surfaces spaced apart by one or more localised index matching regions that form said one or more apertures.

14. An article of manufacture comprising a computer usable medium having a computer readable program code configured to operate the apparatus according to claim 6.

15. A high resolution optical imaging apparatus, comprising:

(i) an illumination system for illuminating, with a multi-wavelength optical beam, a volume of a sample to be imaged in three spatial dimensions;

(ii) a sampling system for sampling, at a two-dimensional grid of sampling points, light reflected or scattered from the illuminated volume of said sample;

(iii) a measurement system for simultaneous capture of phase and amplitude information over a range of wavelengths of the sampled reflected or scattered light, over said two-dimensional grid of sampling points; and (iv) a processor for processing the phase and amplitude information to construct, using digital refocusing, a three-dimensional image of an optical characteristic of said sample over said illuminated volume, wherein said optical characteristic is selected from the group consisting of phase, reflectivity, refractive index, refractive index changes and attenuation, and wherein:

said illumination system is adapted to illuminate said volume with beams incident at two or more incident angles;

said measurement system comprises an interferometer adapted to measure said phase and amplitude information in a single shot at least for each incident angle; and said processor is adapted to: register and stitch together in the Fourier Domain the measurements from the two or more incident angles to create an extended Fourier Field of measurements; and generate said three-dimensional image by Fourier Transformation or digital processing of the extended Fourier Field measurements.

16. The apparatus according to claim 15, wherein said illumination system is adapted to illuminate the sample volume sequentially with said beams incident at two or more incident angles.

17. The apparatus according to claim 15, wherein said illumination system is adapted to illuminate the sample volume simultaneously with said beams incident at two or more incident angles.

18. The apparatus according to claim 15, wherein said sampling system comprises a two-dimensional lenslet array, and said interferometer comprises a two-dimensional sensor array and a wavelength dispersive element for dispersing the light from each of said sampling points onto said sensor array, wherein the lenslets of said lenslet array are positioned with respect to said wavelength dispersive element such that, in use, the light from each of said sampling points is dispersed onto a set of pixels of said sensor array.

19. The apparatus according to claim 18, wherein said two-dimensional lenslet array is positioned so as to sample said signals in the Fourier plane.

20. The apparatus according to claim 18, wherein said two-dimensional lenslet array comprises a rectilinear array of lenslets angled with respect to the dispersive axis of said wavelength dispersive element.

21. An article of manufacture comprising a computer usable medium having a computer readable program code configured to operate the apparatus according to claim 15.

22. A method for performing high resolution optical imaging of a sample, said method comprising the steps of:
 (i) illuminating, with a multi-wavelength optical beam, a volume of a sample to be imaged in three spatial dimensions;
 (ii) sampling, at a two-dimensional grid of sampling points, light reflected or scattered from the illuminated volume of said sample;
 (iii) simultaneously capturing phase and amplitude information over a range of wavelengths of the sampled reflected or scattered light, over said two-dimensional grid of sampling points; and
 (iv) processing the phase and amplitude information to construct, using digital refocusing, a three-dimensional image of an optical characteristic of said sample over said illuminated volume,
 wherein said optical characteristic is selected from the group consisting of phase, reflectivity, refractive index, refractive index changes and attenuation, and wherein:
 first and second images of said optical characteristic are constructed from first and second measurements of said phase and amplitude information captured in single exposures a predetermined time period apart;
 said first image is registered to said second image to determine a spatially resolved phase shift caused by motion or distortion of said sample in any spatial dimension; and
 at least a component of the displacement of said sample associated with said motion or distortion is determined from said phase shift.

23. An article of manufacture comprising a computer usable medium having a computer readable program code configured to implement the method according to claim 22.

24. A method for performing high resolution optical imaging of a sample, said method comprising the steps of:
 (i) illuminating, with a multi-wavelength optical beam, a volume of a sample to be imaged in three spatial dimensions;
 (ii) sampling, at a two-dimensional grid of sampling points, light reflected or scattered from the illuminated volume of said sample;
 (iii) simultaneously capturing phase and amplitude information over a range of wavelengths of the sampled reflected or scattered light, over said two-dimensional grid of sampling points; and
 (iv) processing the phase and amplitude information to construct, using digital refocusing, a three-dimensional image of an optical characteristic of said sample over said illuminated volume,
 wherein said optical characteristic is selected from the group consisting of phase, reflectivity, refractive index, refractive index changes and attenuation, and wherein:
 said volume is illuminated with multi-wavelength light of at least a first polarisation state;
 a first set of simultaneous measurements of said phase and amplitude information over a range of wavelengths, for at least first and second polarisation states, is captured; and
 said first set of simultaneous measurements is processed to generate a three-dimensional representation of one or more polarisation properties of the illuminated volume of said sample.

25. An article of manufacture comprising a computer usable medium having a computer readable program code configured to implement the method according to claim 24.

26. A method for performing high resolution optical imaging of a sample, said method comprising the steps of:
 (i) illuminating, with a multi-wavelength optical beam, a volume of a sample to be imaged in three spatial dimensions;
 (ii) sampling, at a two-dimensional grid of sampling points, light reflected or scattered from the illuminated volume of said sample;
 (iii) simultaneously capturing phase and amplitude information over a range of wavelengths of the sampled reflected or scattered light, over said two-dimensional grid of sampling points; and
 (iv) processing the phase and amplitude information to construct, using digital refocusing, a three-dimensional image of an optical characteristic of said sample over said illuminated volume,
 wherein said optical characteristic is selected from the group consisting of phase, reflectivity, refractive index, refractive index changes and attenuation, and wherein:
 said volume is illuminated with beams incident at two or more incident angles;
 said phase and amplitude information is measured interferometrically in a single shot at least for each incident angle;
 the measurements from the two or more incident angles are registered and stitched together in the Fourier Domain to create an extended Fourier Field of measurements; and
 said three-dimensional image is generated by Fourier Transformation or digital processing of the extended Fourier Field measurements.

27. An article of manufacture comprising a computer usable medium having a computer readable program code configured to implement the method according to claim 26.

28. A high resolution optical imaging apparatus, comprising:
 (i) an illumination system for illuminating, with a multi-wavelength optical beam, a volume of a sample to be imaged in three spatial dimensions;
 (ii) a sampling system for sampling, at a two-dimensional grid of sampling points, light reflected or scattered from the illuminated volume of said sample;
 (iii) a measurement system for simultaneous capture of phase and amplitude information over a range of wavelengths of the sampled reflected or scattered light, over said two-dimensional grid of sampling points; and (iv) a processor for processing the phase and amplitude information to construct, using digital refocusing, a three-dimensional image of an optical characteristic of said sample over said illuminated volume, wherein said optical characteristic is selected from the group consisting of phase, reflectivity, refractive index, refractive index changes and attenuation, and wherein said apparatus is adapted to:

construct, from first and second measurements of said phase and amplitude information captured in single exposures a predetermined time period apart, first and second images of said optical characteristic;

register said first image to said second image to determine a spatially resolved shift caused by motion or distortion of said sample in any spatial dimension; and determine from said shift at least a component of the displacement of said sample associated with said motion or distortion.

\* \* \* \* \*